(12) United States Patent
Hara et al.

(10) Patent No.: US 9,428,777 B2
(45) Date of Patent: Aug. 30, 2016

(54) TRANSFORMANT AND METHOD FOR PRODUCING SAME, AND METHOD FOR PRODUCING LACTIC ACID

(71) Applicant: Asahi Glass Company, Limited, Tokyo (JP)

(72) Inventors: Futoshi Hara, Tokyo (JP); Shuichiro Kimura, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/627,967

(22) Filed: Feb. 20, 2015

(65) Prior Publication Data

US 2015/0232895 A1 Aug. 20, 2015

Related U.S. Application Data

(63) Continuation of application No. PCT/JP2013/072219, filed on Aug. 20, 2013.

(30) Foreign Application Priority Data

Aug. 24, 2012 (JP) ................... 2012-185680

(51) Int. Cl.
*C12P 7/56* (2006.01)
*C12N 1/15* (2006.01)
*C12N 15/00* (2006.01)
*C12N 15/81* (2006.01)
*C12N 9/04* (2006.01)

(52) U.S. Cl.
CPC ............... *C12P 7/56* (2013.01); *C12N 9/0006* (2013.01); *C12N 15/815* (2013.01); *C12Y 101/01027* (2013.01)

(58) Field of Classification Search
None
See application file for complete search history.

(56) References Cited

U.S. PATENT DOCUMENTS

2005/0112737 A1  5/2005 Liu et al.
2012/0214214 A1* 8/2012 Hara ................... C12N 9/0006
                                                              435/139

FOREIGN PATENT DOCUMENTS

JP   2007-512018 A    5/2007
WO  WO-2005/052174 A2  6/2005
WO  WO-2011/021629 A1  2/2011

OTHER PUBLICATIONS

UniProt Accession No. P56511, Apr. 2012, 3 pages.*
L-lactate dehydrogenase 1 (L-LDH 1) [Lactobacillus pentosus MP-10], Database DDBJ/EMBL/GenBank Accession No. CCB83368.1, Aug. 2011.
L-lactate dehydrogenase 1 (L-LDH 1) [Lactobacillus pentosus IG1], Database DDBJ/EMBL/GenBank Accession No. CCC16600.1, Sep. 2011.
Futishi Hara et al., 32rd Annual Meeting of the Molecular Biology Society of Japan, Yoshishu, 2009, 3P-0890, (entire text).
Futishi Hara et al., Abstracts of the 61st Annual Meeting of the Society for Biotechnology, Japan, 2009, p. 190, 2Mp08. (Entire text).
Hayao Taguchi et al., D-Lactate Dehydrogenase Is a Member of the D-Isomer-specific 2-Hydroxyacid Dehydrogenase Family, The Journal of Biological Chemistry, 1991, vol. 266, No. 19, pp. 12588-12594, figure 4.
International Search Report issued in PCT/JP2013/072219 dated Nov. 5, 2013.

* cited by examiner

*Primary Examiner* — David J Steadman
(74) *Attorney, Agent, or Firm* — Foley & Lardner LLP

(57) ABSTRACT

Objects of the present invention are to provide a transformant which can produce lactic acid with high productivity without requiring neutralization with an alkali, a method for producing the same, and a method for producing lactic acid by using the transformant. Namely, they are a transformant, in which *Schizosaccharomyces pombe* is used as a host, a lactate dehydrogenase gene of *Lactobacillus pentosus* is introduced, and a part of a gene cluster encoding a pyruvate decarboxylase in the *Schizosaccharomyces pombe* host is deleted or inactivated; a method for producing the transformant; and a method for producing lactic acid by using the transformant.

13 Claims, 8 Drawing Sheets

TRANSFORMANT AND METHOD FOR PRODUCING SAME, AND METHOD FOR PRODUCING LACTIC ACID

CROSS REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/072219 filed on Aug. 20, 2013, which is based upon and claims the benefit of priority of Japanese Application No. 2012-185680 filed on Aug. 24, 2012, the entire contents of which are hereby incorporated by reference in their entireties.

TECHNICAL FIELD

The present invention relates to a transformant, a method for producing same, and a method for producing lactic acid. In more detail, the present invention relates to a transformant in which a lactate dehydrogenase gene of *Lactobacillus pentosus* is introduced into *Schizosaccharomyces pombe* (hereinafter "*S. pombe*") and a part of a gene cluster encoding a pyruvate decarboxylase is deleted or inactivated, a method for producing the transformant, and a method for producing lactic acid including culturing the transformant in a culture solution and obtaining lactic acid from the culture solution.

This application claims priority based on Japanese Patent Application No. 2012-185680 filed in Japan on Aug. 24, 2012, the contents of which are incorporated by reference herein.

SEQUENCE LISTING

The instant application contains a Sequence Listing which has been submitted electronically in ASCII format and is hereby incorporated by reference in its entirety. Said ASCII copy, created on Mar. 24, 2015, is named 063459-0183_SL.txt and is 58,215 bytes in size.

BACKGROUND ART

Lactic acid is broadly used for application in food, and for application in chemical raw materials such as of medical treatments and cosmetics. Also, polylactic acid which is obtained by using lactic acid is drawing attention as a biodegradable plastic which is degraded finally into carbon dioxide and water by a microorganism and the like. Because of this, it is necessary to produce lactic acid with a low cost and a high productivity.

As the method for producing lactic acid, there is known a biological method in which it is produced by fermenting a sugar by a lactic acid bacterium. However, since lactic acid bacteria have low acid resistance, in order to obtain a high productivity by this method, it is necessary to convert the lactic acid produced by the fermentation into a lactic acid salt by neutralizing it with an alkali. Since such the neutralization with an alkali requires a step for restoring lactic acid from the lactic acid salt, the production process becomes complex and the production cost also becomes high.

As a method for obtaining lactic acid without carrying out neutralization with an alkali, there is a method using a transformant in which a gene encoding a lactate dehydrogenase is introduced into a yeast. For example, PTL 1 discloses that lactic acid can be produced with high productivity without carrying out a neutralization step with an alkali by culturing a transformant in which a lactate dehydrogenase gene derived from a mammal such as a human is introduced into *S. pombe*, and a part of a gene cluster encoding a pyruvate decarboxylase in the *S. pombe* host is deleted or inactivated. Further, PTL 2 discloses that lactic acid can be obtained by culturing a transformant in which an L-lactate dehydrogenase gene of *Lactobacillus plantarum* is introduced into *Saccharomyces cerevisiae* which essentially does not produce ethanol when it is cultured in a culture medium.

RELATED ART REFERENCES

Patent Literature

PTL 1: WO 2011/021629
PTL 2: JP-T-2007-512018

SUMMARY OF INVENTION

Technical Problem

The transformant described in PTL 1 is suited for the production of lactic acid in the presence of a high concentration of a sugar and is also suited for high density fermentation, and can produce lactic acid with unprecedentedly high efficiency without carrying out a neutralization step with an alkali. However, in order to industrially stably produce lactic acid by using a microorganism, it is preferred that there are two or more types of yeasts having a lactic acid productivity equal to or higher than the transformant described in PTL 1.

Accordingly, objects of the present invention are a transformant of *S. pombe* which can produce lactic acid with high productivity without requiring neutralization with an alkali and a method for producing the transformant.

Further another object is a method for producing lactic acid with high productivity without carrying out a neutralization step with an alkali by using the transformant.

In the present invention, the lactic acid refers to L-lactic acid which can be obtained by a biological method.

Solution to Problem

The transformant according to a first aspect of the present invention is characterized in that *S. pombe* is used as a host, a lactate dehydrogenase gene of *Lactobacillus pentosus* is introduced, and a part of a gene cluster encoding a pyruvate decarboxylase in the *S. pombe* host is deleted or inactivated.

In the transformant according to the first aspect of the present invention, preferably, a human lactate dehydrogenase gene is further introduced. Further, in the transformant, the gene encoding a pyruvate decarboxylase which is deleted or inactivated is preferably PDC2 gene. Still further, the lactate dehydrogenase gene is preferably introduced into a chromosome of the *S. pombe*.

Further, the method for producing a transformant according to a second aspect of the present invention is a method for producing a transformant in which a lactate dehydrogenase gene of *Lactobacillus pentosus* is introduced, and a part of a gene cluster encoding a pyruvate decarboxylase is deleted or inactivated, characterized by including: introducing an expression cassette into a host by using *S. pombe* as the host and by using a vector having the expression cassette which contains a promoter and a terminator which function in *S. pombe*, and a lactate dehydrogenase gene of *Lactoba*- cillus pentosus, to obtain the transformant; and using, as the host, a host in which a part of a gene cluster encoding a pyruvate decarboxylase is deleted or inactivated, or deleting or inactivating a part of a gene cluster encoding a pyruvate decarboxylase of the obtained transformant.

In the method for producing a transformant according to the second aspect of the present invention, it is preferred that as the host, a host in which a human lactate dehydrogenase gene is introduced, and a part of a gene cluster encoding a pyruvate decarboxylase is deleted or inactivated is used, or the obtained transformant is introduced thereinto a human lactate dehydrogenase gene, and thereafter a part of a gene cluster encoding a pyruvate decarboxylase of the transformant is deleted or inactivated.

Further, it is also possible to obtain a transformant by introducing an expression cassette into a host by using a transformant obtained by the method for producing a transformant as the host and by using a vector having the expression cassette which contains a promoter and a terminator which function in *S. pombe*, and a human lactate dehydrogenase gene. Still further, it is preferred that the vector further has a recombination region for carrying out a homologous recombination in a chromosome of *S. pombe*, and the expression cassette is introduced into the chromosome of *S. pombe* by using this vector.

Further, in the method for producing a transformant, the gene encoding a pyruvate decarboxylase which is deleted or inactivated is preferably PDC2 gene.

Further, the method for producing lactic acid according to a third aspect of the present invention includes culturing the transformant in a culture solution and obtaining lactic acid from the culture solution.

In the method for producing lactic acid according to the third aspect of the present invention, the culturing is preferably carried out by using a culture solution containing glucose at a concentration of 1 to 50% by mass. In addition, the culturing is preferably further continued after pH of the culture solution becomes 3.5 or less due to the lactic acid produced by the transformant. Further, the transformant in the culture solution preferably has an initial cell density of 0.1 to 5 g (dry cell weight basis)/L. Still further, the culturing is preferably continued without neutralizing the lactic acid in the culture solution, which was produced by the transformant, and also the lactic acid is preferably separated from the culture solution without neutralizing the lactic acid in the culture solution.

Advantageous Effects of Invention

The transformant of *S. pombe* according to the first aspect of the present invention can produce lactic acid with high productivity without requiring neutralization with an alkali. In addition, it is suited for the production of lactic acid in the presence of a high concentration of a sugar, particularly glucose, fructose, sucrose, or maltose, and is also suited for high density culturing.

The transformant can be conveniently obtained by the method for producing a transformant according to the second aspect of the present invention.

In addition, the method for producing lactic acid according to the third aspect of the present invention can produce lactic acid with high productivity without carrying out a neutralization step with an alkali.

That is, the transformant and the method for producing lactic acid using the same according to the present invention can produce lactic acid with high productivity even at a low pH without carrying out neutralization with an alkali, and therefore they can be favorably used as an industrial production process for lactic acid.

DESCRIPTION OF EMBODIMENTS

[Transformant A]

Figure 1:
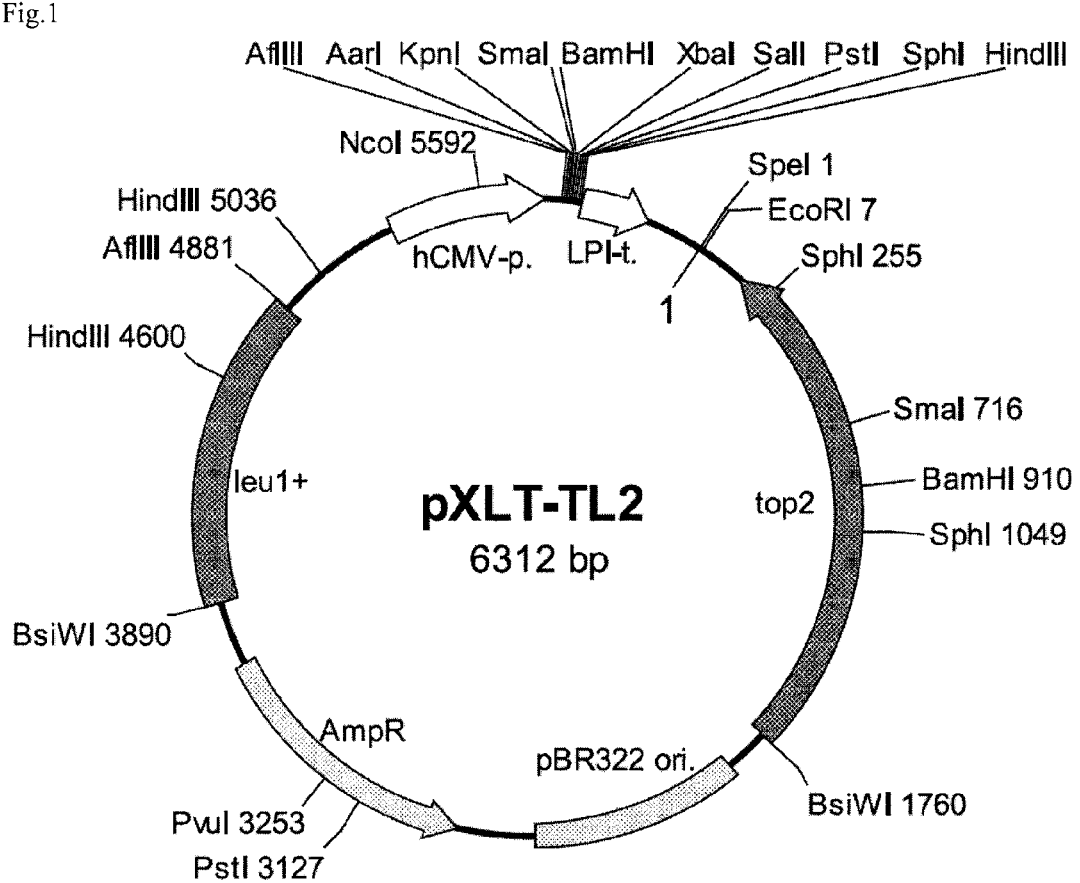
FIG. 1 is a schematic view of a structure of a recombinant vector pXLT-TL2.

The transformant according to the first aspect of the present invention (hereinafter "transformant A") is a transformant in which *Schizosaccharomyces pombe* (hereinafter also referred to as *S. pombe*) is used as a host, a lactate dehydrogenase gene of *Lactobacillus pentosus* is introduced, and a part of a gene cluster encoding a pyruvate decarboxylase in the *S. pombe* host is deleted or inactivated.

<*S. pombe*>

*S. pombe* used as the host is a species of yeast belonging to the genus *Schizosaccharomyces* (fission yeast) and is a microorganism which has particularly excellent acid resistance in comparison with other species of yeast. It was also found that *S. pombe* has excellent productivity of lactic acid in a high concentration of glucose and is also suited for high density culturing (culturing by using a large amount of yeast) in comparison with other species of yeast such as

*Saccharomyces cerevisiae*. Therefore, by using a transformant of *S. pombe*, lactic acid can be produced with extremely high productivity.

In this connection, the entire base sequence of the *S. pombe* chromosome is recorded and disclosed to the public in the database "GeneDB" of the Sanger Institute as "*Schizosaccharomyces pombe* Gene DB". The sequence data of the *S. pombe* genes described in this specification can be obtained by retrieval based on the gene name or the above-mentioned systematic name from the above-mentioned database.

<Gene Encoding Pyruvate Decarboxylase>

The cluster of genes encoding a pyruvate decarboxylase (pyruvate decarboxylase genes, hereinafter also referred to as "PDC genes") in *S. pombe* includes four types of genes: a gene encoding pyruvate decarboxylase 1 (hereinafter referred to as "PDC1 gene"), a gene encoding pyruvate decarboxylase 2 (hereinafter referred to as "PDC2 gene"), a gene encoding pyruvate decarboxylase 3 (hereinafter referred to as "PDC3 gene"), and a gene encoding pyruvate decarboxylase 4 (hereinafter referred to as "PDC4 gene"). Among these, the PDC2 gene and the PDC4 gene are the PDC genes which have major functions in *S. pombe*. The systematic names of the respective PDC genes are as follows.

PDC1 gene (Pdc1); SPAC13A11.06
PDC2 gene (Pdc2); SPAC1F8.07c
PDC3 gene (Pdc3); SPAC186.09
PDC4 gene (Pdc4); SPAC3G9.11c The sequence data of the PDC genes described above can be obtained by retrieval based on the gene name or the systematic name from the above-mentioned *S. pombe* gene database.

In wild-type *S. pombe*, ethanol fermentation is carried out by metabolizing glucose to pyruvic acid through the glycolytic pathway, converting the pyruvic acid to acetaldehyde by a pyruvate decarboxylase expressed by the above-mentioned PDC genes, and then converting the acetaldehyde to ethanol by an alcohol dehydrogenase. In addition, the wild-type *S. pombe* does not have a functional lactate dehydrogenase gene (a gene encoding a lactate dehydrogenase (LDH), hereinafter also referred to as "LDH gene"), and therefore a pathway for producing lactic acid from pyruvic acid is not present.

On the other hand, an LDH expressed by an introduced LDH gene reduces pyruvic acid to lactic acid to produce lactic acid. Therefore, even if an LDH gene is introduced into wild-type *S. pombe* so as to be able to produce lactic acid, the productivity of lactic acid is not sufficiently increased because both ethanol fermentation and lactic acid fermentation proceed if it is as such.

The transformant A according to the present invention has a chromosome in which a part of the above-mentioned gene cluster encoding a pyruvate decarboxylase is deleted or inactivated. Due to the deletion or inactivation of a part of the PDC gene cluster of the transformant, the ethanol fermentation efficiency of the transformant is lowered and the amount of pyruvic acid to be converted to ethanol is reduced, and thus, the productivity of lactic acid is improved. However, when the PDC gene cluster is completely deleted or inactivated, the ethanol fermentation cannot be carried out at all, and thus, the growth is inhibited. Accordingly, the PDC gene cluster to be deleted or inactivated is limited to a part thereof.

It is particularly preferable that the PDC gene to be deleted or inactivated is the PDC2 gene. The PDC2 gene is a PDC gene which has a particularly main function.

As described in the foregoing, when the PDC genes are completely deleted or inactivated, the transformant cannot carry out the ethanol fermentation, and thus, the growth thereof is inhibited. Accordingly, deletion or inactivation of the PDC genes must be carried out in such a manner that an ethanol fermentation capacity necessary for the growth is maintained so that sufficient amount of the transformant can be obtained and also that the ethanol fermentation capacity is lowered so that the fermentation efficiency of lactic acid can be improved. The present inventors have carried out an examination on this problem and found as a result that when the PDC2 gene is deleted or inactivated, the PDC 4 gene is activated to a certain degree so that the ethanol fermentation capacity of such a degree that sufficient amount of the transformant can be obtained and the production of lactic acid with a high fermentation efficiency can become compatible.

Deletion or inactivation of the PDC gene can be carried out by a conventionally known method. For example, the PDC gene can be deleted by using the Latour method (described in Nucleic Acids Res., 2006, vol. 34, p. e11; WO 2007/063919; and the like).

In addition, the PDC gene can be inactivated by causing deletion, insertion, substitution or addition in a part of the base sequence of the PDC gene. Regarding these mutations by deletion, insertion, substitution or addition, only one of them may be conducted or two or more thereof may be conducted.

Regarding the method for introducing the aforementioned mutation into a part of the PDC gene, a conventionally known method can be used. For example, there may be mentioned a mutation separation method in which a mutagen is used (Koubo Bunshi Idengaku Jikken-hou (Methods for Yeast Molecular Genetics Experimentation), 1996, Gakkai Shuppan Center), a random mutation method which makes use of PCR (polymerase chain reaction) (PCR Methods Appl., 1992, vol. 2, p. 28-33) or the like.

In addition, the PDC gene in which a mutation is introduced into a part thereof may be one which expresses a temperature-sensitive mutant-type pyruvate decarboxylase. The temperature-sensitive mutant-type pyruvate decarboxylase is an enzyme which exhibits an activity equivalent to that of the wild-type pyruvate decarboxylase at a certain culture temperature but loses or decreases its activity at a specific culture temperature or higher.

A mutant which expresses such the mutant-type pyruvate decarboxylase can be obtained by selecting a strain which exhibits a growth rate equivalent to the wild-type yeast under such conditions that the activity is not restricted by the temperature but considerably decreases in the growth rate under specific temperature conditions in which the activity is restricted.

<LDH Gene>

The transformant A according to the present invention has an LDH gene. As described above, *S. pombe* does not have an LDH gene by nature. Therefore, the transformant is obtained by introducing an LDH gene of an organism other than *S. pombe* into *S. pombe* by a genetic engineering technique.

The transformant A according to the present invention has an LDH gene of *Lactobacillus pentosus* (LpLDH) (GenBank accession number: D90340). In this connection, GenBank is a database of NCBI (National Center for Biotechnology Information).

The number of LpLDH genes to be introduced into the transformant A according to the present invention may be one, or two or more. It is considered that by introducing two or more LDH genes, the LDH gene expression efficiency can be increased and as a result, the lactic acid production efficiency can be improved.

The transformant A according to the present invention may have another introduced LDH gene derived from another biological species in addition to the LpLDH gene. However, as described in Examples below, there are limited LDH genes capable of providing a transformant which produces lactic acid by introducing the LDH gene into a transformant of S. pombe in which a part of the PDC gene cluster is deleted or inactivated. Examples of the LDH gene derived from another biological species include an LDH gene of a mammal such as a human and an LDH gene of Pediococcus acidilactici (PaLDH gene) (GenBank accession number: Q59645). Among these, a human LDH gene (HsLDH gene) is preferred. By introducing the LpLDH gene and the HsLDH gene in combination, the ability to produce lactic acid is significantly improved in comparison with the case where the same number of HsLDH genes are introduced.

[Production of Transformant]

The transformant A according to the present invention can be obtained by using the S. pombe in which a part of the PDC gene cluster is deleted or inactivated as the host and introducing the LpLDH gene into this S. pombe by a genetic engineering technique. In addition, the transformant A according to the present invention can also be obtained by using the S. pombe in which the PDC gene cluster is neither deleted nor inactivated as the host, introducing the LpLDH gene into this S. pombe by a genetic engineering technique to obtain a transformant, and then deleting or inactivating a part of the PDC gene cluster of the thus obtained transformant. In Examples described below, the target transformant was produced by the former method, but substantially the same transformant can also be produced by the latter method.

In the case where both of the LpLDH gene and the HsLDH gene are introduced into the transformant A according to the present invention, the transformant can be obtained by using a transformant obtained by the above-mentioned method (that is, a transformant of S. pombe in which the LpLDH gene is introduced and also a part of the PDC gene cluster is deleted or inactivated) as the host, and the HsLDH gene is introduced into the transformant by a genetic engineering technique. Further, a transformant of S. pombe in which the HsLDH gene is introduced and also a part of the PDC gene cluster is deleted or inactivated may be used as the host, and the LpLDH gene may be introduced into the transformant of S. pombe by a genetic engineering technique. Still further, a transformant in which both of the LpLDH gene and the HsLDH gene are introduced among the transformants A according to the present invention can also be obtained by using an S. pombe in which the PDC gene cluster is neither deleted nor inactivated as the host, introducing the LpLDH gene and the HsLDH gene simultaneously or sequentially (in random order) into this S. pombe by a genetic engineering technique to obtain a transformant, and then deleting or inactivating a part of the PDC gene cluster of the thus obtained transformant.

Hereinafter, the method for producing the transformant is described by exemplifying a method in which an S. pombe in which a part of the PDC gene cluster is deleted or inactivated is used as the host, and the LpLDH gene (according to need, both of the LpLDH gene and the HsLDH gene) is introduced thereinto by a genetic engineering technique.

<Host>

The S. pombe to be used as the host may be a wild type or a mutant in which a specific gene is deleted or inactivated according to the intended use. As a method for deleting or inactivating a specific gene, a conventionally known method can be used. Specifically, a gene can be deleted by using the Latour method (described in Nucleic Acids Research, vol. 34, p. e11, 2006; WO 2007/063919; and the like). Further, by introducing a mutation into a part of a gene by using a mutation separation method in which a mutagen is used (Koubo Bunshi Idengaku Jikken-hou (Methods for Yeast Molecular Genetics Experimentation), 1996, Gakkai Shuppan Center), a random mutation method which makes use of PCR (polymerase chain reaction) (PCR Methods Application, vol. 2, pp. 28-33 1992,) or the like, the gene can be inactivated. The yeast host of the genus Schizosaccharomyces in which a specific gene is deleted or inactivated is described in, for example, WO 2002/101038, WO 2007/015470, and the like.

Further, the part to be deleted or inactivated of the specific gene may be an ORF (open reading frame) region, or an expression regulatory sequence region. A particularly preferred method is a method for deletion or inactivation by a PCR-mediated homologous recombination method (Yeast, vol. 14, pp. 943-951, 1998) in which the ORF region of a structural gene is substituted with a marker gene.

A mutant in which the PDC gene is deleted or inactivated can be preferably used as the host for producing the transformant A according to the present invention. Further, an S. pombe in which a specific gene other than the PDC gene is further deleted or inactivated in addition to the PDC gene can also be used as the host. By deleting or inactivating a protease gene or the like, the heterologous protein expression efficiency can be increased, and therefore, by applying it as the host in the present invention, the lactic acid production efficiency can be expected to be improved.

In addition, as the S. pombe to be used as the host, it is preferred to use one having a marker for selecting a transformant. For example, it is preferred to use a host for which a specific nutrient component is essential for growth due to deletion of a certain gene. In the case where a transformant is prepared by carrying out transformation by a vector containing a target gene sequence, by introducing this deleted gene (auxotrophic complementation marker) into the vector in advance, the auxotrophy of the host disappears in the transformant. By this difference in auxotrophy between the host and the transformant, these two can be distinguished, and thus, the transformant can be obtained.

For example, a yeast strain of the genus Schizosaccharomyces which is auxotrophic for uracil due to deletion or inactivation of an orotidine 5'-phosphate decarboxylase gene (ura4 gene) is used as the host, and transformation is carried out by using an expression vector having the ura4 gene (auxotrophic complementation marker), and thereafter a strain in which the auxotrophy for uracil disappeared is selected, whereby a transformant into which the expression vector is introduced can be obtained. The gene which causes auxotrophy due to its deletion in the host is not limited to the ura4 gene as long as it can be used in the selection of transformants, and it may be an isopropyl malate dehydrogenase gene (leu1 gene) or the like.

In addition, an S. pombe in which the PDC gene cluster is neither deleted nor inactivated can also be used as a host for the production of a transformant. As the host in this case, one in which a gene as described above other than the PDC gene (an auxotrophic marker, a protease gene, or the like) is deleted or inactivated can be used. After a transformant is produced by using this host, a part of the PDC gene cluster of the thus obtained transformant is deleted or inactivated, whereby the transformant A according to the present invention can be obtained.

<Method for Introducing LDH Gene>

As the method for introducing an LDH gene into a host by a genetic engineering technique, a conventionally known method can be used. As a method in which *S. pombe* is used as the host and a structural gene of a heterologous protein is introduced thereinto, for example, the method described in JP-A-5-15380, WO 95/09914, JP-A-10-234375, JP-A-2000-262284, JP-A-2005-198612, WO 2011/021629, or the like can be used.

<Expression Cassette>

The expression cassette is a combination of DNAs necessary for expressing a target protein and contains a structural gene encoding the target protein, and a promoter and a terminator which function in the host. In the production of the transformant A according to the present invention, each of the expression cassettes of the LpLDH gene or the HsLDH gene contains the LpLDH gene or the HsLDH gene, a promoter which functions in *S. pombe* and a terminator which functions in *S. pombe*. The expression cassette may contain at least either one of a 5'-untranslated region and a 3'-untranslated region. It may further contain the above-mentioned auxotrophic complementation marker. A preferred expression cassette is an expression cassette which contains an LDH gene, a promoter, a terminator, a 5'-untranslated region, a 3'-untranslated region, and an auxotrophic complementation marker. Two or more LDH genes may be present in the same expression cassette. The number of LDH genes in the same expression cassette is preferably from 1 to 8, and more preferably from 1 to 5. Further, in the case where two or more LDH genes are contained in the same expression cassette, two or more types of LDH genes (for example, one or more LpLDH genes and one or more HsLDH genes) may be contained.

As a gene sequence of the LpLDH gene or the HsLDH gene to be contained in the expression cassette, a wild-type gene sequence may be used as it is, however, for increasing the expression level in *S. pombe* to be used as the host, a wild-type gene sequence may be altered to a codon which is frequently used in *S. pombe*.

The promoter and the terminator which function in *S. pombe* may be any as long as they can function in the transformant and maintain the expression of LDH even when it becomes acidic (even when the pH becomes 6 or less) due to accumulation of lactic acid by the transformant A according to the present invention. As the promoter which functions in *S. pombe*, a promoter originally possessed by *S. pombe* (a promoter having a high transcription initiation activity is preferred) or a promoter which is not originally possessed by *S. pombe* (a virus-derived promoter or the like) can be used. In this connection, two or more types of promoters may be present in the vector.

As the promoter originally possessed by *S. pombe*, for example, there may be mentioned an alcohol dehydrogenase gene promoter, an nmt1 gene promoter concerned in thiamin metabolism, a fructose-1,6-bisphosphatase gene promoter concerned in glucose metabolism, an invertase gene promoter concerned in catabolite inhibition (cf., WO 99/23223), a heat shock protein gene promoter (cf., WO 2007/26617), and the like.

As the promoter which is not originally possessed by *S. pombe*, for example, there may be mentioned the animal cell virus-derived promoters described in JP-A-5-15380, JP-A-7-163373 and JP-A-10-234375, of which an hCMV promoter and an SV40 promoter are preferable.

As the terminator which functions in *S. pombe*, a terminator originally possessed by *S. bombe* and a terminator which is not originally possessed by *S. pombe* can be used. In this connection, two or more terminators may be present in the vector.

As the terminator, for example, there may be mentioned the human-derived terminators described in JP-A-5-15380, JP-A-7-163373 and JP-A-10-234375, of which a human lipocortin I terminator is preferable.

<Expression Vector A>

The transformant A according to the present invention has the expression cassette containing the LpLDH gene or both of the expression cassette containing the LpLDH gene and the expression cassette containing the HsLDH gene in a chromosome or as an extrachromosomal gene. To have the expression cassette in a chromosome refers to that the expression cassette is introduced at one or more sites in a chromosome of a host cell, and to have the expression cassette as an extrachromosomal gene refers to that a plasmid containing the expression cassette is contained in a cell. A transformant having the expression cassette containing the LpLDH gene and a transformant having the expression cassette containing the HsLDH gene each can be obtained by transforming *S. pombe* as the host by using an expression vector having each expression cassette.

Hereinafter, the expression vector having the expression cassette containing an LDH gene is sometimes referred to as "expression vector A" according to the present invention.

The expression vector A can be produced by introducing the expression cassette into a vector having a circular DNA structure or a linear DNA structure. As described below, when a transformant which has the expression cassette as an extrachromosomal gene in the host cell is produced, the expression vector A is preferably a plasmid containing a sequence for replication in yeast of the genus *Schizosaccharomyces*, that is, an autonomously replicating sequence (ARS), and when a transformant in which the expression cassette is introduced into a chromosome of the host cell is produced, the expression vector A is preferably introduced into the host cell as one which has a linear DNA structure and does not have an ARS. For example, the expression vector A may be a vector composed of a linear DNA or may be a vector having a circular DNA structure containing a restriction enzyme recognition sequence for being cut open into a linear DNA when it is introduced into the host. In addition, the expression vector A preferably has a marker for selecting a transformant as described below. Examples of the marker include an ura4 gene (auxotrophic complementation marker) and an isopropyl malate dehydrogenase gene (leu1 gene).

Each LDH gene is preferably introduced into a chromosome of *S. pombe*. By introducing an LDH gene into a chromosome, a transformant having excellent subculturing stability can be obtained. In addition, it is also possible to introduce two or more LDH genes into a chromosome. In the transformant A according to the present invention, the number of LpLDH genes introduced into a chromosome is preferably from 1 to 20, and particularly preferably from 1 to 8. Further, when the transformant A according to the present invention also has the HsLDH gene, the number of HsLDH genes introduced into a chromosome of the transformant is preferably from 1 to 20, and particularly preferably from 1 to 8.

As the method for introducing an LDH gene into a chromosome, a conventionally known method can be used.

For example, two or more LDH genes can be introduced into a chromosome by the method described in the abovementioned JP-A-2000-262284. It is also possible to introduce one LDH gene into a chromosome by this method. In addition, as described below, it is also possible to introduce one LDH gene or two or more LDH genes at two or more sites in a chromosome.

As the method for introducing the LpLDH gene or the HsLDH gene into a chromosome of *S. pombe*, a method for introducing such a gene by a homologous recombination method by using a vector which has an expression cassette containing each LDH gene and a recombination region is preferred.

The recombination region of the vector is a region having a base sequence which can carry out homologous recombination with the target region of the homologous recombination in the *S. pombe* chromosome. Also, the target region is a region which becomes a target for introducing the expression cassette into the *S. pombe* chromosome. The target region can be freely arranged by setting the recombination region of the vector to such a base sequence that it can undergo homologous recombination with the target region.

It is necessary that homology of the aforementioned base sequence of the recombination region with the base sequence of the target region is 70% or more. Also, from the viewpoint of causing homologous recombination easily, homology of the base sequence of the recombination region with the base sequence of the target region is preferably 90% or more, and more preferably 95% or more. By the use of a vector having such the recombination region, the expression cassette is introduced into the target region by homologous recombination.

It is preferable that the length (the number of bases) of recombination region is from 20 to 2000 bp. When the length of the recombination region is 20 bp or more, homologous recombination easily occurs. Also, when the length of the recombination region is 2000 bp or less, it becomes easy to prevent difficulty in occurring homologous recombination due to too long size of the vector. The length of recombination region is more preferably 100 bp or more, and further preferably 200 bp or more. Also, the length of recombination region is more preferably 800 bp or less, and is further preferably 400 bp or less.

The expression vector A may have another DNA region in addition to the aforementioned expression cassette and recombination region. For example, there may be mentioned a replication initiation region called "ori" which is necessary for replication in *Escherichia coli* and antibiotics resistance genes (neomycin resistance gene and the like). These are genes which are generally required when a vector is constructed by using *Escherichia coli*. However, it is preferable that the above-mentioned replication initiation region is removed when the vector is introduced into a chromosome of a host as described later.

In the case where an LDH gene is introduced into a chromosome, it is preferred that the expression vector A is introduced into an *S. pombe* cell as a linear DNA structure. That is, in the case of a vector having a circular DNA structure such as a generally used plasmid DNA, it is preferred that after the vector is cut open to become linear with a restriction enzyme, it is introduced into an *S. pombe* cell.

In this case, the position where the vector having a circular DNA structure is cut open is within the recombination region. According to this, the recombination region is partially present in each of both ends of the cut-open vector so that the entire vector is introduced into a target region of a chromosome by homologous recombination.

The expression vector A may be constructed by a method other than the method in which a vector having a circular DNA structure is cut open as long as a linear DNA structure in which a part of the recombination region is present in each of both ends thereof can be formed.

As the expression vector A, for example, an *Escherichia coli*-derived plasmid such as pBR322, pBR325, pUC118, pUC119, pUC18, or pUC19 can be suitably used.

In this case, it is preferable that, at the time when the plasmid vector is used in homologous recombination, a replication initiation region called "ori" which is necessary for replication in *Escherichia coli* is removed therefrom. By this, when the above-mentioned vector is introduced into a chromosome, its introduction efficiency can be improved.

The construction method of the vector from which the replication initiation region is removed is not particularly limited, but it is preferable to use the method described in JP-A-2000-262284. That is, preferred is a method in which a precursor vector in which the replication initiation region is inserted into a cutting position of the recombination region is constructed in advance, so that a linear DNA structure can be obtained in the aforementioned manner and, at the same time, the replication initiation region is cutout. By this, the vector from which the replication initiation region has been removed can be obtained conveniently.

In addition, it may be a method for obtaining a vector to be used in homologous recombination, in which a precursor vector having an expression cassette and a recombination region is constructed by applying the expression vectors or their construction methods described in JP-A-5-15380, JP-A-7-163373, WO 96/23890, JP-A-10-234375 and the like, and then the replication initiation region is removed from the precursor vector by a general genetic engineering technique.

<Target Region>

The target region into which the expression vector A is introduced may be present at only one site or may be present at two or more sites in a chromosome of *S. pombe*. When the target region is present at two or more sites, the vector can be introduced at two or more sites in a chromosome of *S. pombe*. Further, when two or more LDH genes are contained in a same expression cassette, two or more LDH genes can be introduced at one site in the target region. Still further, the expression cassette can also be introduced into two or more kinds of target regions by using two or more kinds of vectors having recombination regions corresponding to the respective target regions. By this method, two or more LDH genes can be introduced into a chromosome of *S. pombe*, and accordingly, the expression level of LDH can be increased and the productivity of lactic acid can therefore be improved. For example, an expression cassette containing the LpLDH gene is introduced into a vector having a first target region, and an expression cassette containing the HsLDH gene is introduced into a vector having a second target region, and an *S. pombe* in which a part of the PDC gene cluster is deleted or inactivated is used as the host and transformed by using the vectors, whereby a transformant also having the HsLDH gene among the transformants A according to the present invention can be obtained.

When the expression cassette is introduced into a target region at one site, for example, the target region described in the method disclosed in JP-A-2000-262284 can be used. By using two or more kinds of vectors having different recombination regions, the vectors can be introduced into the respective different target regions. However, this method is complicated when vectors are introduced into two or more sites in a chromosome.

When mutually and substantially identical base sequence moieties presenting in two or more sites in a chromosome are used as target regions and vectors can be introduced into the respective two or more sites of target regions, vectors can be introduced into two or more sites in the chromosome by using one kind of the vector. The mutually and substantially identical base sequences mean that homology of the base sequences is 90% or more. It is preferable that homology between the target regions is 95% or more. In addition, the length of mutually and substantially identical base sequences is a length which includes the recombination region of the aforementioned vector and is preferably 1000 bp or more. In comparison with the case in which two or more LDH genes are introduced into one site of target region, when the LDH genes are introduced in a distributed manner into two or more target regions present even when the number of introduced LDH genes is the same, it is rare that the LDH genes are dropped out of the chromosome at one time when the transformant grows, so that maintaining stability of the transformant in subculturing is improved.

As the target region which is present in two or more sites in a chromosome, a transposon gene Tf2 is preferable. It is known that the Tf2 is a transposon gene which is present at a total of 13 sites respectively in 3 (haploid) chromosomes of *S. pombe*, its length (the number of basis) is about 4900 bp and the base sequence homology among these genes is 99.7% (cf., the following reference).

Nathan J. Bowen et al., "Retrotransposons and Their Recognition of pol II Promoters: A Comprehensive Survey of the Transposable Elements From the Complete Genome Sequence of *Schizosaccharomyces pombe*", Genome Res., 2003, 13: 1984-1997

A vector can be introduced into only one site of Tf2 present in 13 sites in a chromosome. In this case, a transformant having two or more of the LDH genes can be obtained by introducing an expression vector A having two or more of the LDH genes. Also, a transformant having two or more of the LDH genes can be obtained by introducing an expression vector A into two or more sites of Tf2. In this case, a transformant having a further large number of the LDH genes can be obtained by introducing an expression vector A having two or more of the LDH genes. When an expression vector A is introduced into all of the 13 sites of Tf2, there is a possibility that load on the survival and growth of the transformant becomes too large. Preferably, it is preferable that an expression vector A is introduced into 8 sites or less of the 13 sites of Tf2 and it is more preferable that an expression vector A is introduced into 5 sites or less thereof.

<Transformation Method>

As the transformation method, any of conventionally known transformation methods can be used. Examples of the transformation method include conventionally well-known methods such as a lithium acetate method [K. Okazaki et al., Nucleic Acids Res., 18, 6485-6489 (1990)], an electroporation method, a spheroplast method, and a glass bead method, and a method described in JP-A-2005-198612. In addition, a commercially available yeast transformation kit may be used.

As the method for transforming the *S. pombe* host by a homologous recombination method, a conventionally known homologous recombination method can be used. As the transformation method in producing the transformant according to the present invention, preferred is a method in which the above-mentioned *S. pombe* in which a part of the PDC gene cluster is deleted or inactivated is used as a host, and an expression cassette is introduced into a chromosome thereof by homologous recombination by using the above-mentioned vector. According to this method, the transformant according to the present invention can be produced conveniently.

In the production of the transformant, in general, after carrying out homologous transformation, the transformants obtained are subjected to selection. Examples of the selection method include the following method. Screening is carried out by using a medium capable of selecting transformants based on the above-mentioned auxotrophic marker, and from the obtained colonies, two or more are selected. Subsequently, after the colonies are separately liquid-cultured, an expression level of a heterologous protein (in the present invention, LpLDH or HsLDH) in each culture solution is examined, and then, transformants showing a higher expression level of the heterologous protein are selected. By carrying out a genomic analysis of these selected transformants by pulse field gel electrophoresis, the number of vectors and the number of expression cassettes introduced into a chromosome can be examined.

The number of vectors to be introduced into a chromosome can be controlled to some extent by controlling the introduction conditions or the like. It is considered that the introduction efficiency and the number of introduced vectors also change depending on the size (the number of bases) or the structure of the vector.

In general, it is expected that the LDH expression efficiency is increased as the number of expression cassettes is increased, and as a result, the lactic acid production efficiency is increased. Therefore, it is considered that the productivity of lactic acid can be improved by introducing two or more LDH genes into a chromosome of *S. pombe* to increase the expression level of LDH. However, it is also considered that when the number of expression cassettes is too large, a load on the survival and growth of cells is increased so that the lactic acid production efficiency may be lowered. On the other hand, by incorporating two or more genes in a same expression cassette, a large number of LDH genes can be introduced into a chromosome while suppressing the number of expression cassettes to be introduced into a chromosome. However, it is considered that when the size of the vector is increased, the probability of being introduced into a chromosome is lowered, and it becomes difficult to increase the number of vectors to be introduced, so that to obtain the transformant is difficult in itself.

Therefore, the present inventors presumed that in order to obtain a transformant of *S. pombe* having higher lactic acid production efficiency even when a relatively small number of expression cassettes with a moderate size are introduced into a chromosome, it is necessary to select and introduce an exogenous LDH gene which has a high expression efficiency in *S. pombe* and expresses LDH whose activity is also high. When LDH genes derived from various microorganisms were examined, it was found that by introducing the LpLDH gene into a transformant of *S. pombe* in which a part of the PDC gene cluster is deleted or inactivated, a transformant having very high lactic acid production efficiency can be obtained like in the case where the HsLDH gene is introduced. More surprisingly, by introducing the LpLDH gene and the HsLDH gene together, a transformant having significantly higher lactic acid production efficiency was obtained as compared with the case where the same number of HsLDH genes were introduced.

[Method for Producing Lactic Acid]

The method for producing lactic acid according to the present invention is a method for producing lactic acid by culturing the transformant A according to the present invention in a culture solution and obtaining lactic acid from the culture solution.

By culturing the transformant A according to the present invention in a culture solution containing a sugar, pyruvic acid obtained from the sugar through the glycolytic pathway is reduced by lactate dehydrogenase to generate lactic acid, and the lactic acid generated into the culture solution is recovered from the culture solution, so that lactic acid can be produced.

Regarding the culture solution to be used in the production of lactic acid, a conventionally known yeast culture medium containing a sugar can be used, and it may further contain a nitrogen source, an inorganic salt and the like which can be assimilated by *S. pombe* and can carry out culturing of *S. pombe* efficiently. As the culture solution, a natural medium may be used or a synthetic medium may be used.

As the sugar as a carbon source, for example, there may be mentioned sugars such as glucose, fructose, sucrose, and maltose. As the nitrogen source, for example, there may be mentioned an ammonia, an ammonium salt of inorganic acid or organic acid such as ammonium chloride and ammonium acetate, a peptone, a casamino acid, an yeast extract, and the like. As the inorganic salts, for example, there may be mentioned magnesium phosphate, magnesium sulfate, sodium chloride, and the like. In addition, a fermentation accelerator such as proteolipid and the like can be contained.

According to the method for producing lactic acid according to the present invention, it is preferable to use a culture solution which contains especially glucose as the sugar. Glucose concentration of the culture solution (100% by mass) in the initial stage of culturing is preferably 1% by mass or more, more preferably from 1 to 50% by mass and further preferably from 2 to 16% by mass. Since the glucose concentration is lowered by the culturing, it is preferable to continue the culturing by adding glucose in response to the necessity. Glucose concentration at the final stage of culturing may become 1% by mass or less. In addition, when the culturing is continuously carried out by circulating the culture solution while separating lactic acid, it is preferable to keep the above-mentioned glucose concentration. By setting the glucose concentration to 2% by mass or more, the productivity of lactic acid is further improved. Also, by setting glucose in the culture solution to 16% by mass or less, the production efficiency of lactic acid is further improved.

In addition, for the purpose of increasing productivity of lactic acid production, it is preferable to carry out a high density culturing. In the high density culturing, it is preferable that an initial cell density of the transformant in the culture solution is set to from 0.1 to 5 g/L, on the dry cell weight basis. It is more preferable that the initial cell density of the transformant in the culture solution is set to from 0.2 to 2 g/L, on the dry cell weight basis. By increasing the initial cell density, a high productivity can be attained within short period of time. In addition, when the initial cell density is too high, there is a possibility of causing a problem such as aggregation of cells or lowering of purification efficiency.

In this connection, the cell density shown in the examples and the like which are described later is a value converted from the absorbance of light having a wavelength of 660 nm (OD660) measured by a visible-ultraviolet spectrometer V550 manufactured by JASCO Corporation. The OD660=1 at 660 nm corresponds to 0.2 g dry weight and 0.8 g wet weight, of the fission yeast.

In the culturing, a conventionally known yeast culturing method can be used, and for example, it can be carried out by a shaking culture, an agitation culture and the like.

In addition, it is preferable that culturing temperature is from 23 to 37° C. Also, culturing time can be optionally determined.

In addition, the culturing may be a batch culture or may be a continuous culture. For example, after carrying out the culturing by a batch culture, a culture solution containing lactic acid can be obtained by separating cells from the culture solution. Also, in the case of a continuous culture method, for example, there may be mentioned a method in which culturing is continuously carried out by repeating the steps of drawing out a part of the culture solution from the culture vessel in the course of culturing and separating lactic acid from the drawn out culture solution, while recovering the culture supernatant and returning the culture supernatant to the culture vessel after adding glucose or fresh culture solution thereto. By carrying out continuous culture, productivity of lactic acid is further improved.

In the method for producing lactic acid by using the transformant A according to the present invention, since *S. pombe* having particularly excellent acid resistance is used, lactic acid can be produced without carrying out neutralization even when pH becomes low (the pH is about 2 to 4) due to the accumulation of the lactic acid. Therefore, also after the pH of the culture solution becomes 3.5 or less, lactic acid can be produced by continuous culture in which the culturing is further continued. The pH at the final stage of culturing or the pH during continuous culture is preferably from 2 to 3.5, and particularly preferably from 2.3 to 3.5. For the purpose of increasing the productivity of lactic acid, it is preferred to further continue the culturing after the pH of the culture solution becomes 3.5 or less. Since the transformant A according to the present invention has excellent acid resistance, the culturing can be continued without neutralizing lactic acid in the culture solution produced by the transformant.

A conventionally known method can be used in obtaining lactic acid from the culture solution. Particularly, it is preferable to obtain lactic acid by separating the culture solution and lactic acid without neutralizing the lactic acid in the culture solution. For example, there may be mentioned a method in which, after separating cells from the culture solution by centrifugation after completion of the culturing and adjusting the pH to 1 or less, extraction is carried out with diethyl ether, ethyl acetate and the like; a method in which, after adsorption to an ion exchange resin and subsequent washing, elution is carried out; a method in which impurities are removed by using activated carbon; a method in which distillation is carried out after allowing to react with an alcohol in the presence of an acid catalyst; and a method in which separation is carried out by using a separation membrane. In addition, in some cases, lactic acid can be obtained by neutralizing the lactic acid in the culture solution and then separating the culture solution and the lactic acid salt. For example, lactic acid can also be obtained by a method in which the lactic acid in the culture solution is converted into calcium salt or lithium salt and this neutralized salt is crystallized.

Since the method for producing lactic acid according to the present invention described in the above uses, as a host, a transformant prepared from *S. pombe* which is particularly excellent in acid resistance, lactic acid can be produced conveniently with a high productivity without carrying out neutralization with an alkali. In addition, since the efficiency of ethanol fermentation is lowered due to deletion or inactivation of a part of the PDC gene cluster, a sugar base yield of lactic acid (ratio of produced amount of lactic acid based on the amount of consumed sugar) is improved. According to the present invention, the sugar base yield of lactic acid can be easily increased to 50% or more. In some cases, the sugar base yield of lactic acid reaches 70% or more. In addition, the method for producing lactic acid according to the present invention is also suited for the high density culturing in the presence of a high concentration of glucose and by a high concentration of the transformant.

EXAMPLES

The following describes the present invention in detail by showing examples and comparative examples. However, the present invention is not restricted by the following descriptions. In this connection, the term "%" as used in these examples means "% by mass" unless otherwise noted.

Example 1

Preparation of PDC2 Gene-Deleted S. pombe Strain

An ARC010 strain (genotype: h-, leu1-32, ura4-D18) (cf., WO 2007/015470), which is a uracil auxotrophic S. pombe strain, was transformed in accordance with the Latour method (described in Nucleic Acids Res., 2006, vol. 34, p. e11, and WO 2007/063919), thereby preparing a gene-deleted strain (IGF543 strain) in which PDC2 gene (systematic name: SPAC1F8.07c) was deleted.

In the preparation of deletion fragments, a complete genomic DNA prepared by using DNeasy (manufactured by QIAGEN, Inc.) from an S. pombe ARC032 strain (genotype: h-) (cf., WO 2007/015470) was used as a template, and 8 types of synthetic oligo DNAs (manufactured by Operon Technologies, Inc.) having each of the base sequences shown in Table 1 were used.

TABLE 1

Oligo DNA for preparation of pdc2 gene-deleted fragments

| Oligo DNA | Base sequence | Sequence No. |
|---|---|---|
| UF | 5'-CTCTCCAGCTCCATCCATAAG-3' | 1 |
| UR | 5'-GACACAACTTCCTACCAAAAAGCCTTTCTGCCCATGTTTTCTGTC-3' | 2 |
| OF | 5'-GCTTTTTGGTAGGAAGTTGTGTC-3' | 3 |
| OR | 5'-AGTGGGATTTGTAGCTAAGCTGTATCCATTTCAGCCGTTTGTG-3' | 4 |
| DF | 5'-AAGTTTCGTCAATATCACAAGCTGACAGAAAACATGGGCAGAAAG-3' | 5 |
| DR | 5'-GTTCCTTAGAAAAAGCAACTTTGG-3' | 6 |
| FF | 5'-CATAAGCTTGCCACCACTTC-3' | 7 |
| FR | 5'-GAAAAAGCAACTTTGGTATTCTGC-3' | 8 |

Specifically, a UP region by using UF and UR, an OL region by using OF and OR, and a DN region by using DF and DR were prepared, respectively, by a PCR method using KOD-Dash (manufactured by Toyobo Co., Ltd.), and then, by using them as templates, full-length deletion fragments were respectively prepared, by a similar PCR method using FF and FR. When preparing the full-length deletion fragments, the two types of synthetic oligo DNAs (manufactured by Operon Technologies, Inc.) having each of the base sequences shown in Table 2 were used, the complete genomic DNA similarly prepared from the ARC032 strain was used as a template, and a ura4 region fragment prepared by a similar PCR method was also used together as a template.

TABLE 2

Oligo DNA for preparation of ura4 gene-deleted fragments

| Oligo DNA | Base sequence | Sequence No. |
|---|---|---|
| F | 5'-AGCTTAGCTACAAATCCCACT-3' | 9 |
| R | 5'-AGCTTGTGATATTGACGAAACTT-3' | 10 |

The obtained PDC2 gene-deleted S. pombe strain (IGF543 strain, h-leu1-32 ura4-D18 pdc2-D23) had a low growth rate. Therefore, in order to restore the growth rate, the IGF543 strain was streaked on YES plate (yeast extract 0.5%/glucose 3%/SP supplement) and cultured at 25° C. The thus obtained colonies were subcultured in YPD medium (yeast extract 1%/peptone 2%/glucose 2%) and cultured at 25° C., and then, by using the well-grown culture solutions, glycerol stocks were prepared and stored at −80° C. By repeating the above-mentioned procedure until an appropriate growth rate was obtained, a strain whose growth rate was restored was prepared (the strain succeeded to the name IGF543).

Example 2

Preparation of S. pombe Strain Introduced One Copy of LDH Gene

Transformant strains of S. pombe into which the HsLDH gene, the LpLDH gene, an LDH gene of Lactobacillus bulgaricus (LbLDH gene) (GenBank accession number: ABJ57783), an LDH gene of Lactobacillus plantarum (LplLDH gene) (GenBank accession number: P59390), the PaLDH gene, or an LDH gene of Staphylococcus aureus (SaLDH gene) (GenBank accession number: Q5HJD7) was introduced were prepared.

Specifically, the IGF543 strain (gene-deleted S. pombe strain) prepared in Example 1 was transformed in accordance with the method of Bahler et al. (Yeast, 1998, vol. 14, pp. 943-951) using restriction enzyme BsiWI digests of a single-locus integration-type recombinant vector having an HsLDH gene expression cassette, pXLT-HsLDH, a single-locus integration-type recombinant vector having an LpLDH gene expression cassette, pXLT-LpLDH, a single-locus integration-type recombinant vector having an LbLDH gene expression cassette, pXLT-LbLDH, a single-locus integration-type recombinant vector having an LplLDH gene expression cassette, pXLT-LplLDH, a single-locus integration-type recombinant vector having a PaLDH gene expression cassette, pXLT-PaLDH, or a single-locus integration-type recombinant vector having an SaLDH gene expression cassette, pXLT-SaLDH.

The pXLT-HsLDH was prepared by the process described below. That is, first, an integration-type vector for fission yeast, pXL4 (Idiris et al., Yeast, 2006, vol. 23, pp. 83-99) was double-digested with restriction enzymes, and the obtained fragment was subjected to a blunt-end treatment, followed by ligation. The thus obtained expression vector for fission yeast, pXL1 (delta-neo) was further double-digested with restriction enzymes, and the obtained fragment was subjected to a blunt-end treatment, followed by insertion of a top2 gene fragment cloned from the ARC010 strain genome, thereby preparing pXLT-TL2 (6312 bp, FIG. 1) having a sequence (5'→3', circular) shown in SEQ ID NO: 11 in the Sequence Listing.

Subsequently, a gene fragment encoding the human L-lactate dehydrogenase structural gene (HsLDH-ORF) described in the literature (Tsujibo et al., Eur. J. Biochem., 1985, vol. 147, pp. 9-15) was amplified by PCR by using, as a template, a human fibroblast cDNA library introduced into the Okayama vector (literature: Okayama, H. and Berg, P.: A cDNA cloning vector that permits expression of cDNA inserts in mammalian cells. Mol. Cell. Biol., 3 (1983), 280-289), and also by using a primer set (HsLDH-F and HsLDH-R, manufactured by Operon Technologies, Inc.) shown in Table 3, in which a restriction enzyme NcoI recognition sequence was added to the 5'-terminal side, and a restriction enzyme SalI recognition sequence was added to the 3'-terminal side. The ORF fragment encoded HsLDH (SEQ ID NO: 14).

TABLE 3

| | Base sequence | Sequence No. |
|---|---|---|
| HsLDH-F | 5'-AAAACCATGGCAACTCTAAAGGATCAGC TGATTTAT-3' | 12 |
| HsLDH-R | 5'-AAAAGGTACCTTAAAATTGCAGCTCCTT TTGGATCCC-3' | 13 |
| HsLDH | MATLKDQLIYNLLKEEQTPQNKITVVGVGAV GMACAISILMKDLADELALVDVIEDKLKGEM MDLQHGSLFLRTPKIVSGKDYNVTANSKLVI ITAGARQQEGESRLNLVQRNVNIFKFIIPNV VKYSPNCKLLIVSNPVDILTYVAWKISGFPK NRVIGSGCNLDSARFRYLMGERLGVHPLSCH GWVLGEHGDSSVPVWSGMNVAGVSLKTLHPD LGTDKDKEQWKEVHKQVVESAYEVIKLKGYT SWAIGLSVADLAESIMKNLRRVHPVSTMIKG LYGIKDDVFLSVPCILGQNGISDLVKVTLTS EEEARLKKSADTLWGIQKELQF | 14 |

The thus obtained amplification fragment was double-digested with restriction enzymes NcoI and SalI and then introduced between the AflIII and SalI sites of the multi-cloning vector pTL2M5 described in JP-A-2000-262284, thereby preparing an LDH expression vector pTL2HsLDH. Further, an expression cassette (hCMV promoter/HsLDH-ORF/LPI terminator) was cut out from the pTL2HsLDH by double digestion with restriction enzymes SpeI and Bst1107I and introduced into pXLT-TL2, thereby preparing pXLT-HsLDH.

The pXLT-LpLDH was prepared by the process described below. That is, first, an ORF fragment of the LpLDH gene was obtained by using, as a template, a complete genomic DNA prepared with DNeasy (manufactured by QIAGEN, Inc.) from a culture of a *Lactobacillus pentosus* NBRC 106467 strain (obtained from NBRC (Biological Resource Center, NITE)), and also by using two types of synthetic oligo DNAs (LpLDH-F and LpLDH-R, manufactured by Operon Technologies, Inc.) shown in Table 4, by a PCR method using KOD-Dash (manufactured by Toyobo Co., Ltd.). The ORF fragment encoded LpLDH (SEQ ID NO: 17).

TABLE 4

| | Sequence | Sequence No. |
|---|---|---|
| LpLDH-F | 5'-AAAACCATGTCAAGCATGCCAAATCATC AAAAAG-3' | 15 |
| LpLDH-R | 5'-AAAAGGTACCTTATTTGTTTTCTAATTC TGCTAAACCGTCG-3' | 16 |
| LpLDH | MSSMPNHQKVVLVGDGAVGSSYAFAMAQQGI AEEFVIVDVVKDRTKGDALDLEDAQAFTAPK KIYSGEYSDCKDADLVVITAGAPQKPGESRL DLVNKNLNILSSIVKPVVDSGFDGIFLVAAN PVDILTYATWKFSGPPKERVIGSGTSLDSSR LRVALGKQFNVDPRSVDAYIMGEHGDSEFAA YSTATIGTRPVRDVAKEQGVSDDDLAKLEDG VRNKAYDIINLKGATFYGIGTALMRISKAIL RDENAVLPVGAYMDGQYGLNDIYIGTPAIIG GTGLKQIIESPLSADELKKMQDSAATLKKVL NDGLAELENK | 17 |

The thus obtained amplification fragment was double-digested with restriction enzymes NcoI and SalI and then introduced between the AflIII and SalI sites of the above-mentioned pTL2M5, thereby preparing an LDH expression vector pTL2LpLDH. Further, an expression cassette (hCMV promoter/LpLDH-ORF/LPI terminator) was cut out from the pTL2LpLDH by double digestion with restriction enzymes SpeI and Bst1107I and introduced into pXLT-TL2, thereby preparing pXLT-LpLDH.

The pXLT-LplLDH was prepared by the process described below. That is, first, an ORF fragment of the LbLDH gene was obtained by using, as a template, a complete genomic DNA prepared with DNeasy (manufactured by QIAGEN, Inc.) from a culture of a *Lactobacillus bulgaricus* NBRC 13953 strain (obtained from NBRC), and also by using two types of synthetic oligo DNAs (LbLDH-F and LbLDH-R, manufactured by Operon Technologies, Inc.) shown in Table 5, by a PCR method using KOD-Dash (manufactured by Toyobo Co., Ltd.).

TABLE 5

| | Sequence | Sequence No. |
|---|---|---|
| LbLDH-F | 5'-CAATTTTATTTATAAACAATGAGTAGAAAA GTCCTGCTGGTTG-3' | 18 |
| LbLDH-R | 5'-CTCTAGAGGATCCCCGGTTATCCTAAAGAG TCCAGGGTTGCC-3' | 19 |

The thus obtained amplification fragment was double-digested with restriction enzymes NcoI and SalI and then introduced between the AflIII and SalI sites of the above-mentioned pTL2M5, thereby preparing an LDH expression vector pTL2LbLDH. Further, an expression cassette (hCMV promoter/LbLDH-ORF/LPI terminator) was cut out from the pTL2LbLDH by double digestion with restriction enzymes SpeI and Bst1107I and introduced into pXLT-TL2, thereby preparing pXLT-LbLDH.

The pXLT-LplLDH was prepared by the process described below. That is, first, an ORF fragment of the LplLDH gene was obtained by using, as a template, a complete genomic DNA prepared with DNeasy (manufactured by QIAGEN, Inc.) from a culture of a *Lactobacillus plantarum* NBRC 15891 strain (obtained from NBRC), and also by using two types of synthetic oligo DNAs (LplLDH-F and LplLDH-R, manufactured by Operon Technologies, Inc.) shown in Table 6 by a PCR method by using KOD-Dash (manufactured by Toyobo Co., Ltd.).

TABLE 6

| Sequence | Sequence No. |
|---|---|
| LplLDH-F 5'-GACACTTTTTCAAACATGATGGATAAGAAGCAACGCAAAGTC-3' | 20 |
| LplLDH-R 5'-CATGTGAAGCAGGTGTTATGATGCCACATTCATCATGGTCAG-3' | 21 |

The thus obtained amplification fragment was double-digested with restriction enzymes NcoI and SalI and then introduced between the AflIII and SalI sites of the above-mentioned pTL2M5, thereby preparing an LDH expression vector pTL2LplLDH. Further, an expression cassette (hCMV promoter/LplLDH-ORF/LPI terminator) was cut out from the pTL2LplLDH by double digestion with restriction enzymes SpeI and Bst1107I and introduced into pXLT-TL2, thereby preparing pXLT-LplLDH.

The pXLT-PaLDH was prepared by the process described below. That is, first, an ORF fragment of the PaLDH gene was obtained by using, as a template, a complete genomic DNA prepared with DNeasy (manufactured by QIAGEN, Inc.) from a culture of a *Pediococcus acidilactici* NBRC 3076 strain (obtained from NBRC), and also by using two types of synthetic oligo DNAs (PaLDH-F and PaLDH-R, manufactured by Operon Technologies, Inc.) shown in Table 7, by a PCR method using KOD-Dash (manufactured by Toyobo Co., Ltd.).

TABLE 7

| Sequence | Sequence No. |
|---|---|
| PaLDH-F 5'-GACACTTTTTCAAACATGATGTCTAATATTCAAAATCATCAAAAAGTTGTCC-3' | 22 |
| PaLDH-R 5'-CATGTGAAGCAGGTGTTATTTGTCTTGTTTTTCAGCAAGAGCG-3' | 23 |

The thus obtained amplification fragment was double-digested with restriction enzymes NcoI and SalI and then introduced between the AflIII and SalI sites of the above-mentioned pTL2M5, thereby preparing an LDH expression vector pTL2PaLDH. Further, an expression cassette (hCMV promoter/PaLDH-ORF/LPI terminator) was cut out from the pTL2PaLDH by double digestion with restriction enzymes SpeI and Bst1107I and introduced into pXLT-TL2, thereby preparing pXLT-PaLDH.

The pXLT-SaLDH was prepared by the process described below. That is, first, an ORF fragment of the SaLDH gene was obtained by using, as a template, a complete genomic DNA prepared with DNeasy (manufactured by QIAGEN, Inc.) from a culture of a *Staphylococcus aureus* NBRC 102135 strain (obtained from NBRC), and also by using two types of synthetic oligo DNAs (SaLDH-F and SaLDH-R, manufactured by Operon Technologies, Inc.) shown in Table 8, by a PCR method using KOD-Dash (manufactured by Toyobo Co., Ltd.).

TABLE 8

| Sequence | Sequence No. |
|---|---|
| SaLDH-F 5'-GACACTTTTTCAAACATGATGAAAACATTTGGTAAAAAGGTTGTATTAATCG-3' | 24 |
| SaLDH-R 5'-CATGTGAAGCAGGTGTTAGTCTTCTAATAAATATTTAATTGAATCAAATGTATCTTCTAATG-3' | 25 |

The thus obtained amplification fragment was double-digested with restriction enzymes NcoI and SalI and then introduced between the AflIII and SalI sites of the above-mentioned pTL2M5, thereby preparing an LDH expression vector pTL2SaLDH. Further, an expression cassette (hCMV promoter/SaLDH-ORF/LPI terminator) was cut out from the pTL2SaLDH by double digestion with restriction enzymes SpeI and Bst1107I and introduced into pXLT-TL2, thereby preparing pXLT-SaLDH.

TABLE 9

| Transformant strain name | Host strain name | Introduced LDH gene name |
|---|---|---|
| ASP3509 | IGF543 | HsLDH |
| ASP3575 | IGF543 | LbLDH |
| ASP3521 | IGF543 | LpLDH |
| ASP3519 | IGF543 | LplLDH |
| ASP3517 | IGF543 | PaLDH |
| ASP3515 | IGF543 | SaLDH |

<Culture Test>

Each of the thus obtained transformants was inoculated into YPD6 liquid medium (yeast extract 1%, peptone 2%, and glucose 6%) and cultured for 24 hours under the conditions that the temperature was 32° C. and the shaking rate was 100 rpm. After completion of the culture, the cells were collected, inoculated into 4.5 mL of an 11.1% glucose aqueous solution at an initial cell density of 36 g (dry cell weight basis)/L, and cultured for 3, 6, or 24 hours under the conditions that the temperature was 32° C. and the shaking rate was 100 rpm. After completion of the culture, the concentrations (g/L) of glucose, ethanol, and lactic acid in the culture solution were measured. The measurement results, and the sugar base yield (selectivity %) and the production rate (g/(L·h)) of lactic acid calculated from the measurement results are shown in Table 10.

TABLE 10

| LDH gene introduced into transformant | Culturing time [h] | Glucose conc. [g/l] | Ethanol conc. [g/l] | Lactic acid conc. [g/l] | Production rate of lactic acid [g/lh] | Sugar base yield of lactic acid [%] |
|---|---|---|---|---|---|---|
| HsLDH | 6.0 | 0.0 | 12.3 | 83.2 | 13.9 | 74.9 |
| LbLDH | 6.0 | 0.0 | 51.9 | 0.0 | 0.0 | 0.0 |
| LpLDH | 3.0 | 7.7 | 9.2 | 78.9 | 26.3 | 76.4 |
| LplLDH | 6.0 | 0.0 | 55.2 | 0.0 | 0.0 | 0.0 |
| PaLDH | 6.0 | 14.5 | 34.7 | 22.0 | 3.7 | 22.8 |
| SaLDH | 24.0 | 35.1 | 35.0 | 0.0 | 0.0 | 0.0 |

Based on these results, the production of lactic acid was confirmed in the ASP3509 strain into which the HsLDH gene was introduced, the ASP3521 strain into which the LpLDH gene was introduced, and the ASP3517 strain into which the PaLDH gene was introduced. In particular, the ASP3521 strain achieved a high sugar base yield comparable to the ASP3509 strain. On the other hand, the production of lactic acid was not confirmed in the ASP3575 strain into which the LbLDH gene was introduced, the ASP3519 strain into which the LplLDH gene was introduced, and the ASP3515 strain into which the SaLDH gene was introduced. In particular, the LplLDH gene is an LDH gene derived from a microorganism belonging to the same genus *Lactobacillus* as the LpLDH gene, and is supposed to be capable of obtaining a lactic acid producing strain by being introduced into *Saccharomyces cerevisiae* (cf., PTL 2). However, a lactic acid producing strain could not be obtained.

Example 3

Preparation of Strain Introduced Two Copies of LDH Gene

Transformants in which an LDH gene derived from the same or different organism was introduced at two sites in a chromosome of the IGF543 strain prepared in Example 1 were prepared, and the ability to produce lactic acid of each of the transformants was examined.

Specifically, first, the IGF543 strain (gene-deleted *S. pombe* strain) prepared in Example 1 was transformed in accordance with the method of Okazaki et al. (Okazaki et al., Nucleic Acids Res., 1990, vol. 18, pp. 6485-6489) by using a Tf2 multilocus integration-type recombinant vector having an HsLDH gene expression cassette, pTf2-HsLDH, a Tf2 multilocus integration-type recombinant vector having an LpLDH gene expression cassette, pTf2-LpLDH, a Tf2 multilocus integration-type recombinant vector having an LbLDH gene expression cassette, pTf2-LbLDH, a Tf2 multilocus integration-type recombinant vector having an LplLDH gene expression cassette, pTf2-LplLDH, a Tf2 multilocus integration-type recombinant vector having a PaLDH gene expression cassette, pTf2-PaLDH, or a Tf2 multilocus integration-type recombinant vector having an SaLDH gene expression cassette, pTf2-SaLDH, thereby preparing *S. pombe* strains introduced one copy of LDH gene, in which one copy of an LDH gene regulated by the hCMV promoter was introduced in the vicinity of the Leu1 locus. A strain in which two copies of the HsLDH gene were introduced was named ASP2914 strain, a strain in which one copy of the LpLDH gene and one copy of the HsLDH gene were introduced was named ASP3631 strain, a strain in which one copy of the LbLDH gene and one copy of the HsLDH gene were introduced was named ASP3619 strain, a strain in which one copy of the LplLDH gene and one copy of the HsLDH gene were introduced was named ASP3622 strain, a strain in which one copy of the PaLDH gene and one copy of the HsLDH gene were introduced was named ASP3623 strain, and a strain in which one copy of the SaLDH gene and one copy of the HsLDH gene were introduced was named ASP3621 strain.

The pTf2-HsLDH was prepared by the process described below. That is, first, a DNA fragment (about 3950 bp) of Tf2-2 (systematic name annotated in GeneDB: SPAC167.08 gene) of *S. pombe* was amplified by a PCR method using a complete genomic DNA of *S. pombe* as a template and also using two types of synthetic oligo DNAs (Tf2-2-F and Tf2-2-R, manufactured by Operon Technologies, Inc.) in which a restriction enzyme BsiWI recognition sequence (CGTACG) was introduced at the 5'-terminal side. The both ends of the amplified DNA fragment were treated with a restriction enzyme BsiWI, thereby preparing an insert fragment.

Aside from this, a vector for chromosomal integration, pXL4 (Idiris et al., Yeast, vol. 23, pp. 83-99, 2006) was digested with the same restriction enzyme BsiWI, thereby obtaining a DNA fragment of a region (about 2130 bp) containing an ampicillin resistance gene (ApR) and an *E. coli* replication origin (pBR322 ori). The fragment was further subjected to a dephosphorylation treatment, thereby preparing a vector fragment.

The insert fragment and the vector fragment were ligated by using a ligase, with which *E. coli* DH5 (manufactured by Toyobo Co., Ltd.) was transformed, and then, a construction vector pTf2-2 (6071 bp) was obtained.

The full length was amplified by a PCR method using the thus obtained construction vector pTf2-2 as a template, and also using a synthetic oligo DNA (MCS-Tf2-2-F, manufactured by Operon Technologies, Inc.) having restriction enzyme KpnI, HindIII, XbaI, and SalI recognition sequences at the 5'-terminal side and a synthetic oligo DNA (MCS-Tf2-2-R, manufactured by Operon Technologies, Inc.) having restriction enzyme KpnI, StuI, XhoI, and NheI recognition sequences at the 5'-terminal side, thereby obtaining a 6060-bp fragment. The both ends of the fragment were digested with KpnI, followed by self-circularization, whereby a 6058-bp vector pTf2 (MCS) further having a multicloning site (MCS) within the transposon gene Tf2-2 sequence was prepared.

Figure 2:
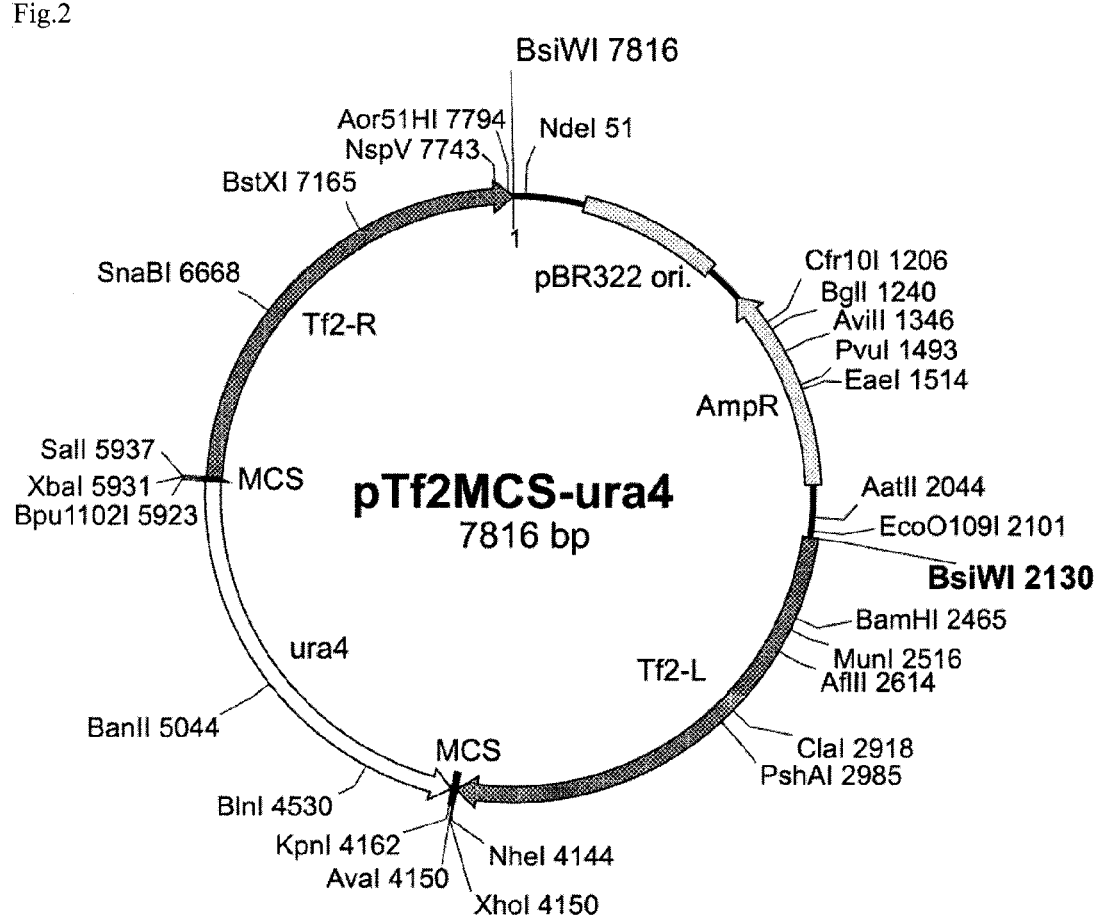
FIG. 2 is a schematic view of a structure of a recombinant vector pTf2(MCS)-ura4.

A fragment in which restriction enzyme KpnI and NheI recognition sequences were added to both ends of a uracil auxotrophic marker ura4 (systematic name annotated in GeneDB: SPCC330.05c, orotidine-5'-phosphate decarboxylase gene) of *S. pombe* was prepared by a PCR method. A 2206-bp fragment obtained by double digestion of the thus prepared fragment with restriction enzymes KpnI and NheI and a 6040-bp fragment obtained by double digestion of the above-prepared construction vector pTf2 (MCS) with restriction enzymes KpnI and NheI were joined by ligation, whereby a 7816-bp Tf2 multilocus integration-type recombinant vector pTf2(MCS)-ura4 (FIG. 2, SEQ ID NO: 30) further having a multicloning site (MCS) and a ura4 region within the transposon gene Tf2-2 sequence was prepared.

TABLE 11

| Sequence | | Sequence No. |
|---|---|---|
| Tf2-2-F | 5'-AAGGCCTCGTACGTGAAAGCAAGAGC AAAACGA-3' | 26 |
| Tf2-2-R | 5'-AAGGCCTCGTACGTGCTTTGTCCGCT TGTAGC-3' | 27 |
| MCS-Tf2-2-F | 5'-GGGGTACCAAGCTTCTAGAGTCGACT CCGGTGCTACGACACTTT-3' | 28 |
| MCS-Tf2-2-R | 5'-GGGGTACCAGGCCTCTCGAGGCTAGC CATTTCCAGCGTACATCCT-3' | 29 |

The expression cassette (hCMV promoter/HsLDH-ORF/LPI terminator) was cut out from the pTL2HsLDH prepared in Example 2 by double digestion with restriction enzymes SpeI and Bst1107I and introduced between the restriction enzyme NheI and KpnI (blunted) recognition sequences of the pTf2(MCS)-ura4, thereby preparing pTf2-HsLDH.

In the same manner, the expression cassettes were cut out from the pTL2LbLDH, pTL2LpLDH, pTL2LplLDH, pTL2PaLDH, and pTL2SaLDH prepared in Example 2 by double digestion with restriction enzymes SpeI and Bst1107I, and each of them was introduced between the restriction enzyme NheI and KpnI (blunted) recognition sequences of the pTf2(MCS)-ura4, thereby preparing pTf2-LbLDH, pTf2-LpLDH, pTf2-LplLDH, pTf2-PaLDH, and pTf2-SaLDH.

Subsequently, the *S. pombe* strain introduced one copy of LDH gene prepared above was transformed in accordance with the method of Okazaki et al. (Okazaki et al., Nucleic Acids Res., 1990, vol. 18, pp. 6485-6489) by using a single-locus integration-type recombinant vector having an HsLDH gene expression cassette, pSL17-HsLDH, thereby preparing an *S. pombe* strain introduced two copies of LDH gene in which further one copy of the HsLDH gene regulated by the ihc promoter was introduced in the vicinity of the Leu1 locus.

The pSL17-HsLDH was prepared by cutting out the ORF fragment of HsLDH from the pTL2HsLDH prepared in Example 2 by double digestion with restriction enzymes NcoI and SalI, and introducing the fragment into a single-locus integration-type recombinant vector pSL17 prepared by the process described below.

Figure 3:
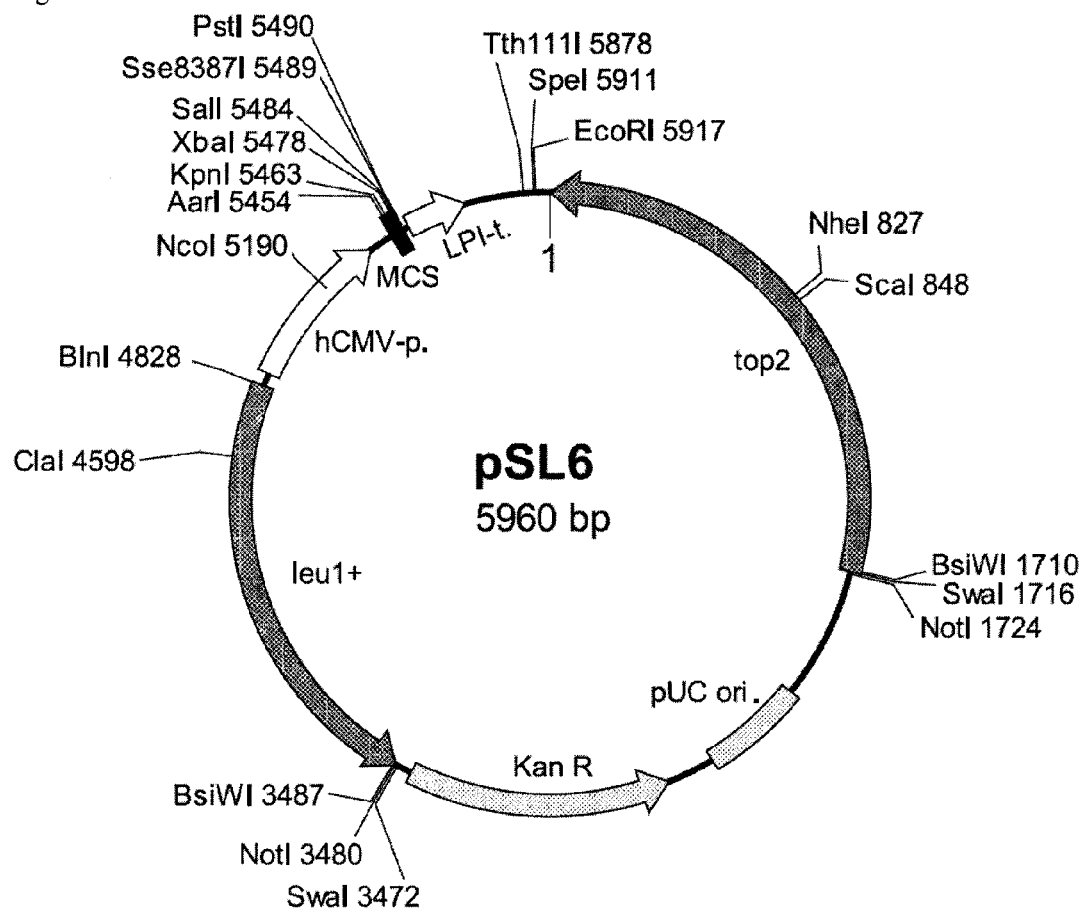
FIG. 3 is a schematic view of a structure of a recombinant vector pSL6.
Figure 4:
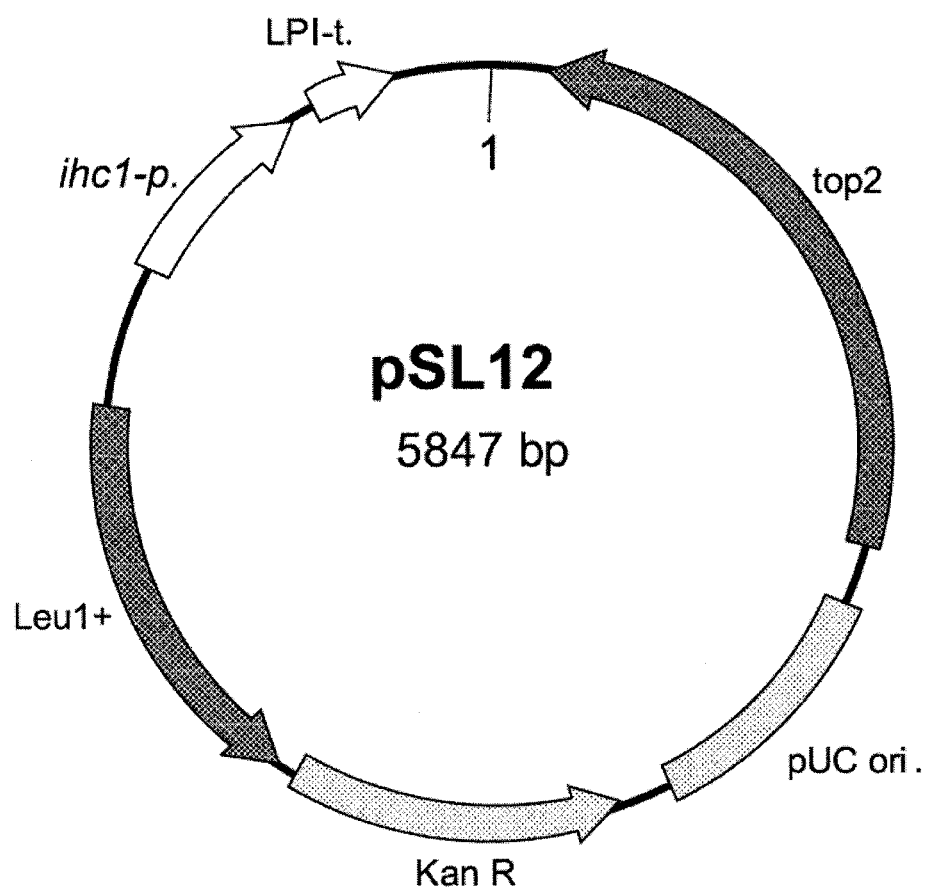
FIG. 4 is a schematic view of a structure of a recombinant vector pSL12.

The single-locus integration-type recombinant vector pSL17 was prepared by the process described below. That is, first, the hCMV promoter region of a conventionally known integration-type vector for fission yeast, pSL6 (FIG. 3, 5960 bp, SEQ ID NO: 31) was substituted with the ihc1 gene promoter (ihc1 promoter) of *S. pombe*, thereby preparing a multicloning vector pSL12 (FIG. 4, 5847 bp).

Specifically, first, a region (SEQ ID NO: 32) from 1 to 501 bp upstream of the 5' end (A of the start codon ATG) of the ORF in the ihc1 gene of *S. pombe* was amplified by PCR by using, as a template, a genomic DNA derived from a wild-type *S. pombe* strain (corresponding to ARC032 strain, ATCC 38366, 972h-), and also by using a forward primer (ihc1-promoter-F) having a BlnI restriction enzyme recognition sequence at the 5' end and a reverse primer (ihc1-promoter-R) having a KpnI restriction enzyme recognition sequence at the 5' end, thereby obtaining a fragment (ihc promoter fragment) having a BlnI restriction enzyme recognition sequence at the 5' end and a KpnI restriction enzyme recognition sequence at the 3' end of the region.

A fragment obtained by double digestion of the ihc promoter fragment with restriction enzymes BlnI and KpnI was introduced into a fragment obtained by double digestion of pSL6 with restriction enzymes BlnI and KpnI by ligation, thereby obtaining an integration-type vector for fission yeast, pSL12 (SEQ ID NO: 35).

Figure 5:
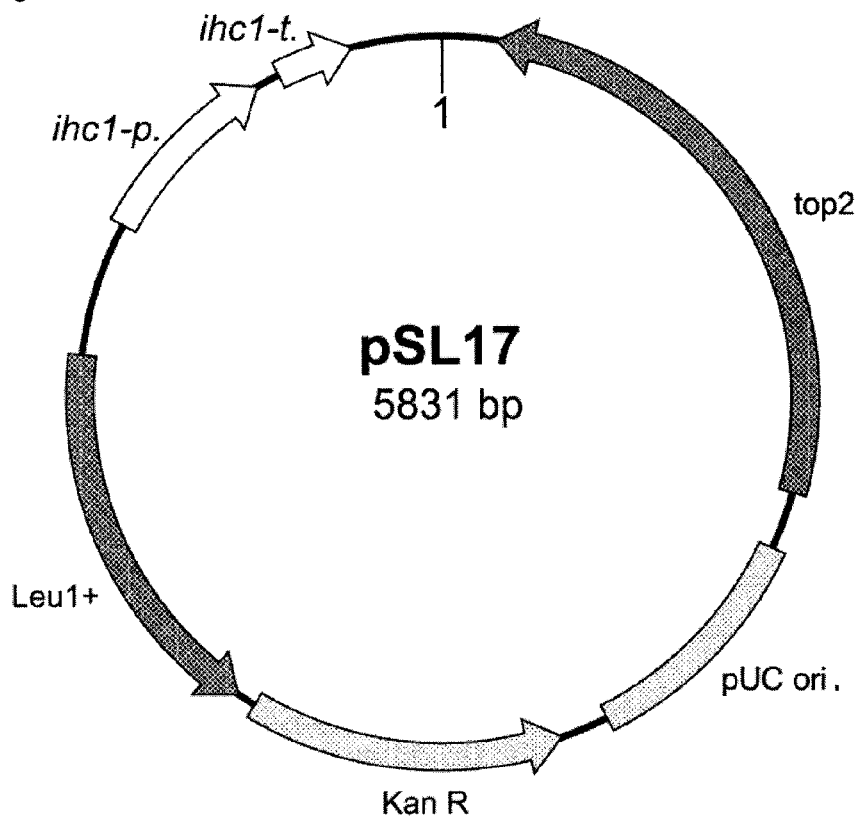
FIG. 5 is a schematic view of a structure of a recombinant vector pSL17.
Figure 6:
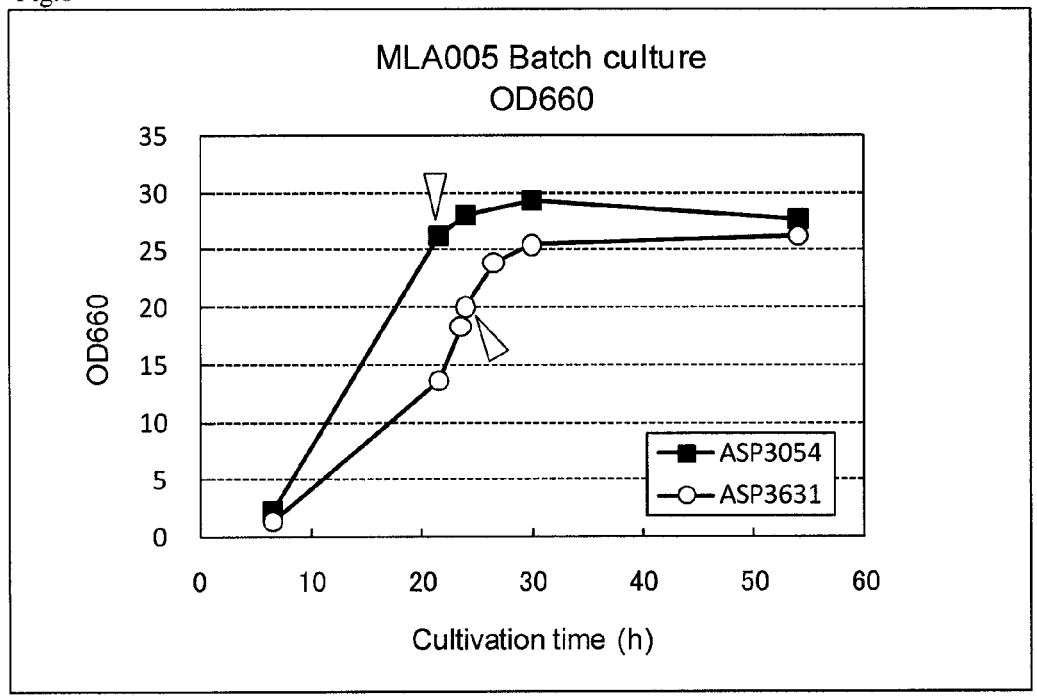
FIG. 6 is a graph showing a change in OD660 over time during jar fermenter culture in [Example 3] in Examples. In the graph, a triangle mark indicates a time point when a small amount of a culture solution containing cells was taken out for use in test tube fermentation.
Figure 7:
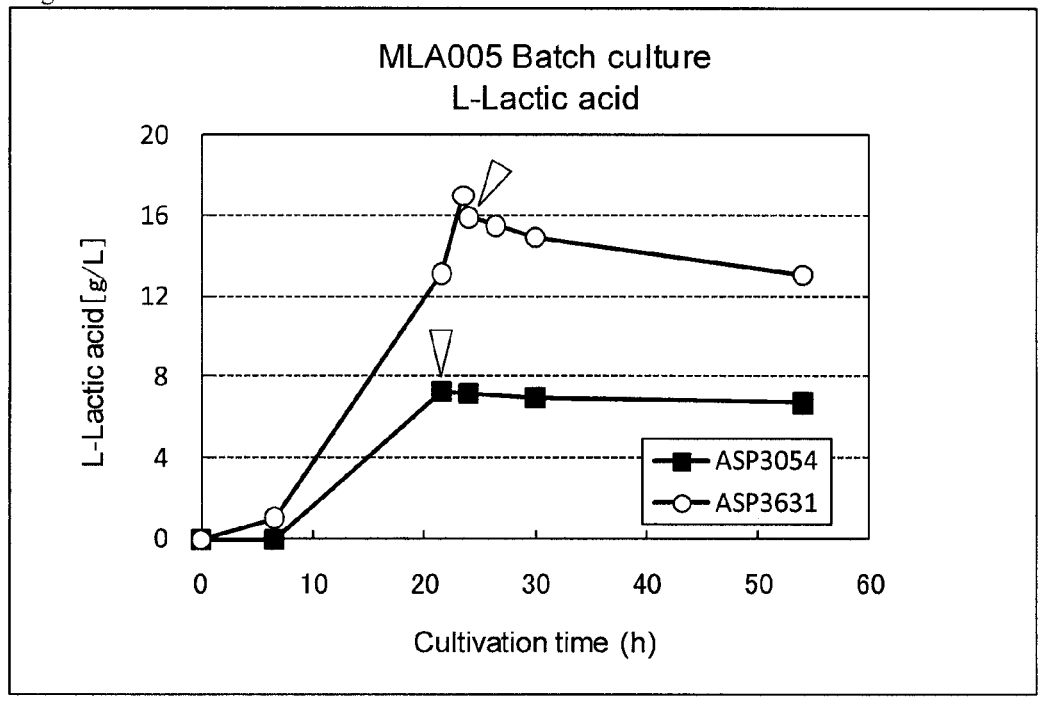
FIG. 7 is a graph showing a change in lactic acid concentration over time during jar fermenter culture in [Example 3] in Examples. In the graph, a triangle mark indicates a time point when a small amount of a culture solution containing cells was taken out for use in test tube fermentation.
Figure 8:
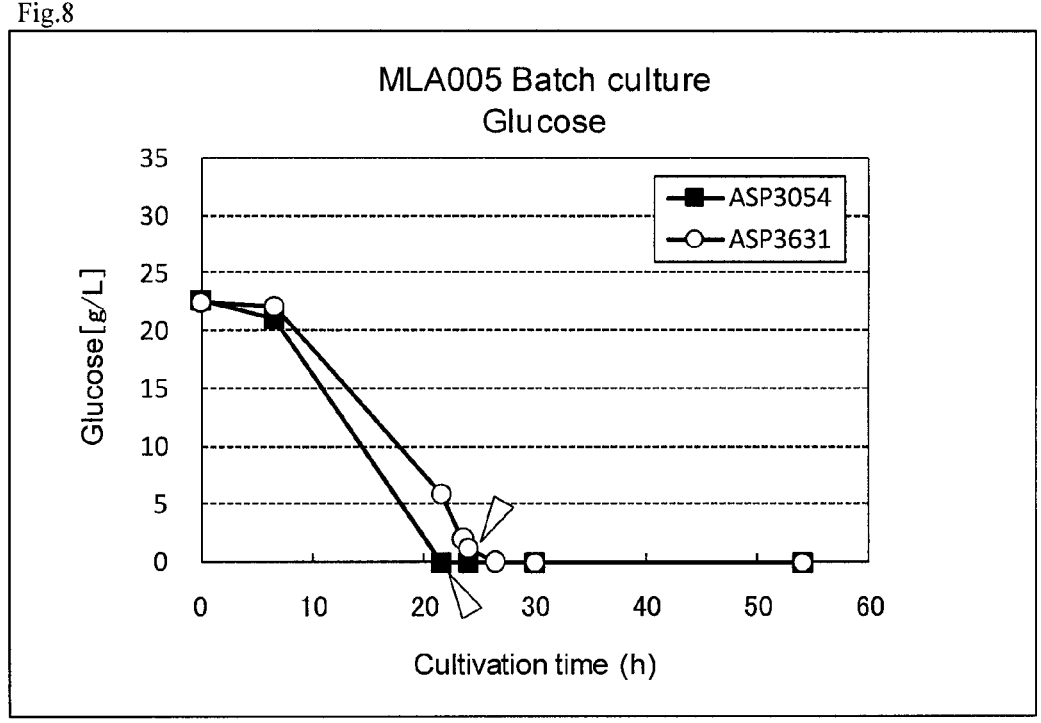
FIG. 8 is a graph showing a change in glucose concentration over time during jar fermenter culture in [Example 3] in Examples. In the graph, a triangle mark indicates a time point when a small amount of a culture solution containing cells was taken out for use in test tube fermentation.
Figure 9:
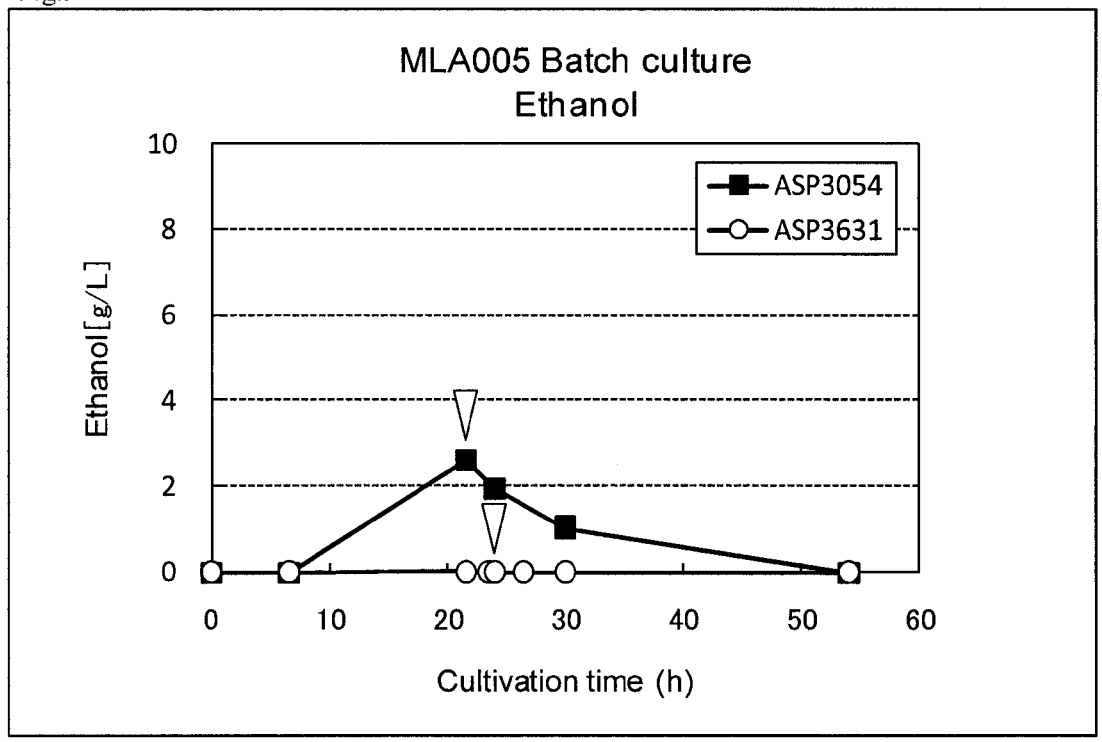
FIG. 9 is a graph showing a change in ethanol concentration over time during jar fermenter culture in [Example 3] in Examples. In the graph, a triangle mark indicates a time point when a small amount of a culture solution containing cells was taken out for use in test tube fermentation.

Subsequently, the LPI terminator region of the pSL12 was substituted with the ihc1 gene terminator (ihc1 terminator) of *S. pombe*, thereby preparing a multicloning vector pSL17 (FIG. 5, 5831 bp).

Specifically, first, a region (SEQ ID NO: 36) from 1 to 200 bp downstream of the 3' end (the third letter of the stop codon) of the ORF in the ihc1 gene of *S. pombe* was amplified by PCR by using, as a template, a genomic DNA derived from a wild-type *S. pombe* strain (corresponding to ARC032 strain, ATCC 38366, 972h-), and also by using In-fusion primers (ihc1-terminator-F and ihc1-terminator-R), thereby obtaining a fragment (ihc terminator fragment) having an ihc terminator region.

A fragment in which the LPI terminator region was deleted from the full-length pSL12 was obtained by carrying out amplification by PCR by using the pSL12 as a template and also by using In-fusion primers (pSL12-F and pSL12-R). The ihc terminator fragment was introduced into the thus obtained fragment by using an In-fusion cloning kit (product name: In-Fusion HD Cloning Kit w/Cloning Enhancer, manufactured by Takara Bio, Inc.), thereby preparing a multicloning vector pSL17 (SEQ ID NO: 41).

TABLE 12

| | Sequence | Sequence No. |
|---|---|---|
| ihc1-promoter-F | 5'-AATTCCTAGGGGCTTCAACTAGCT CGGGAT-3' | 33 |
| ihc1-promoter-R | 5'-AATTGGTACCGACACCTGCTTCAC ATTGTTTATAAATAAAATTGGAGTT-3' | 34 |
| ihc1-terminator-F | 5'-CCTGCAGGCATGCAAGCTTATTGC TGCCCAGTTGATTACCC-3' | 37 |
| ihc1-terminator-R | 5'-GAAACGCGCGAGGCAGATCATTGT ATGCTATGGGGTGTCGAC-3' | 38 |
| pSL12-F | 5'-GTCGACACCCCATAGCATACAATG ATCTGCCTCGCGCGTTTC-3' | 39 |
| pSL12-R | 5'-GGGTAATCAACTGGGCAGCAATAA GCTTGCATGCCTGCAGG-3' | 40 |

<Preparation of Strain Introduced One Copy of HsLDH Gene>

As a strain for comparison when measuring the ability to produce lactic acid of the prepared strain introduced two copies of LDH gene, a strain introduced one copy of HsLDH gene was prepared.

Specifically, the IGF543 strain (gene-deleted *S. pombe* strain) prepared in Example 1 was transformed in accordance with the method of Bahler et al. (Yeast, 1998, vol. 14, pp. 943-951) by using a restriction enzyme BsiWI digest of the single-locus integration-type recombinant vector having an HsLDH gene expression cassette and also having the ihc1 promoter, pSL17-HsLDH, thereby preparing a transformant strain in which one copy of the HsLDH gene regulated by the ihc promoter was introduced in the vicinity of the Leu1 locus. The thus prepared transformant strain was named ASP3509 strain.

<Culture Test>

In the same manner as in Example 2, each strain was inoculated into YPD 6 liquid medium and cultured. Then, the collected cells were cultured in an 11.1% glucose aqueous solution. After completion of the culture, the concentrations (g/L) of glucose, ethanol, and lactic acid in the culture solution were measured. The cultivation time and the measurement results, and the sugar base yield (selectivity, %) and the production rate (g/(L·h)) of lactic acid calculated from the measurement results are shown in Table 13 and Table 14.

TABLE 13

| Transformant strain name | LDH gene introduced into transformant | Culturing time [h] | Glucose conc. [g/l] | Ethanol conc. [g/l] | Lactic acid conc. [g/l] | Production rate of lactic acid [g/(lh)] | Sugar base yield of lactic acid [%] |
|---|---|---|---|---|---|---|---|
| ASP3509 | HsLDH | 3.0 | 15.3 | 10.1 | 76.1 | 25.4 | 68.6 |
| ASP2914 | HsLDH/HsLDH | 3.0 | 15.4 | 8.9 | 78.3 | 26.1 | 70.5 |
| ASP3619 | HsLDH/LbLDH | 3.0 | 19.0 | 10.2 | 72.2 | 24.1 | 65.0 |
| ASP3631 | HsLDH/LpLDH | 3.0 | 7.5 | 6.1 | 91.5 | 30.5 | 82.5 |

TABLE 13-continued

| Transformant strain name | LDH gene introduced into transformant | Culturing time [h] | Glucose conc. [g/l] | Ethanol conc. [g/l] | Lactic acid conc. [g/l] | Production rate of lactic acid [g/(lh)] | Sugar base yield of lactic acid [%] |
|---|---|---|---|---|---|---|---|
| ASP3622 | HsLDH/LplLDH | 3.0 | 23.4 | 11.7 | 64.8 | 21.6 | 58.4 |
| ASP3623 | HsLDH/PaLDH | 3.0 | 15.9 | 11.3 | 73.1 | 24.4 | 65.9 |
| ASP3621 | HsLDH/SaLDH | 3.0 | 18.7 | 10.2 | 72.5 | 24.2 | 65.3 |

TABLE 14

| Transformant strain name | LDH gene introduced into transformant | Culturing time [h] | Glucose conc. [g/l] | Ethanol conc. [g/l] | Lactic acid conc. [g/l] | Sugar base yield of lactic acid [%] |
|---|---|---|---|---|---|---|
| ASP3509 | HsLDH | 5.0 | 0.0 | 13.0 | 80.0 | 72.1 |
| ASP2914 | HsLDH/HsLDH | 5.0 | 0.0 | 5.5 | 85.4 | 77.0 |
| ASP3631 | HsLDH/LpLDH | 10.5 | 0.0 | 5.0 | 93.7 | 84.5 |

As a result, the sugar base yield of lactic acid at the time point when the 3-hour cultivation time passed was 68.6% in the ASP3509 strain in which only one copy of the HsLDH gene was introduced, and 70.5% in the ASP2914 strain in which two copies of the HsLDH gene were introduced. Therefore, it was found that the ability to produce lactic acid was slightly increased in the case of the strain introduced two copies than in the case of the strain introduced one copy. On the other hand, the sugar base yield of lactic acid in the ASP3619 strain, the ASP3622 strain, the ASP3623 strain, and the ASP3621 strain were all lower than in the case of the ASP3509 strain. In particular, in the ASP3622 strain in which one copy of the LplLDH gene were introduced in combination, the ability to produce lactic acid was apparently lowered as compared with the ASP3509 strain. On the other hand, in the ASP3631 strain in which one copy of the HsLDH gene and one copy of the LpLDH gene were introduced, the sugar base yield of lactic acid was 82.5%, and the ability to produce lactic acid was significantly improved as compared with the ASP3509 strain and the ASP2914 strain.

Further, when the ASP3509 strain, the ASP2914 strain, and the ASP3631 strain, each of which achieved a high sugar base yield of lactic acid, were further continued to be cultured, as shown in Table 14, the sugar base yield of lactic acid was 72.1% in the ASP3509 strain, 77.0% in the ASP2914 strain, and 84.5% in the ASP3631 strain.

With respect to the HsLDH gene and the LpLDH gene, in the case where only one copy was introduced into the IGF543 strain, the ability to produce lactic acid was nearly equal in both cases, however, in a strain in which one copy of the HsLDH gene and one copy of the LpLDH gene were introduced, the ability to produce lactic acid was significantly higher than a strain in which two copies of the HsLDH gene were introduced. The reason for this is not clear, however, this is presumed to be because, by the coexistence of HsLDH and LpLDH in the same yeast, some kind of synergistic effect is obtained.

<Culture Test in Jar Fermenter and Test Tube Fermentation Test>

The ASP3631 strain prepared above which is a strain introduced two copies and the ASP3054 strain which is a strain introduced one copy described in WO 2012/114979 were compared with respect to the ability to produce lactic acid and evaluated. A fermentation test was carried out by using cells cultured in a jar fermenter as a system closer to the actual production.

Inoculation of the ASP3054 strain or the ASP3631 strain into 5 mL of YES medium (pH 4.5) in a test tube was carried out, and shaking culture (preculture) was carried out at 32° C. for 24 hours by using 20 test tubes for each strain.

Subsequently, by using 2-L jar fermenters (2 fermenters), 100 mL of the culture solution of each strain obtained by the preculture was added to 900 mL of YPD medium in each fermenter, and culture was started at 30° C. The pH was maintained at 4.5 by control with addition of 10 N KOH. The stirring rotation speed was cascade controlled based on the dissolved oxygen concentration (DO), and the DO was maintained at 1 ppm.

A portion of the culture solution was taken out at the time point when glucose in the medium was consumed, and a fermentation test in a test tube was carried out. The culture test was continued until the 54th hour. The results of the measured OD660 value of the culture solution, and the concentrations (g/L) of lactic acid, glucose and ethanol are shown in FIG. 6, FIG. 7, FIG. 8, and FIG. 9.

The results of the jar fermenter culture showed that as compared with the ASP 3054 strain, the ASP3631 strain had a slightly lower cell growth rate, but produced almost no ethanol and exhibited a doubled amount of produced L-lactic acid. While the ASP3631 strain tended to have a slightly decreased cell growth potential, it was confirmed that the metabolism of glucose to lactic acid was strengthened.

Figure 10:
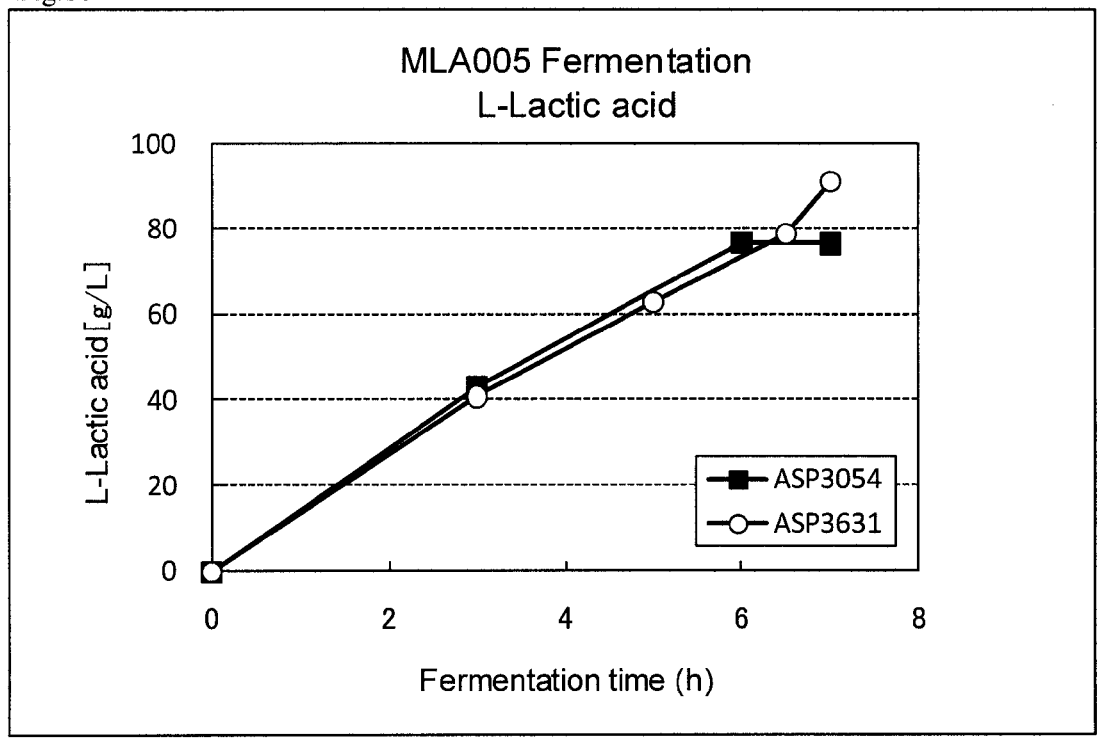
FIG. 10 is a graph showing a change in lactic acid concentration over time during the test tube fermentation in [Example 3] in Examples.
Figure 11:
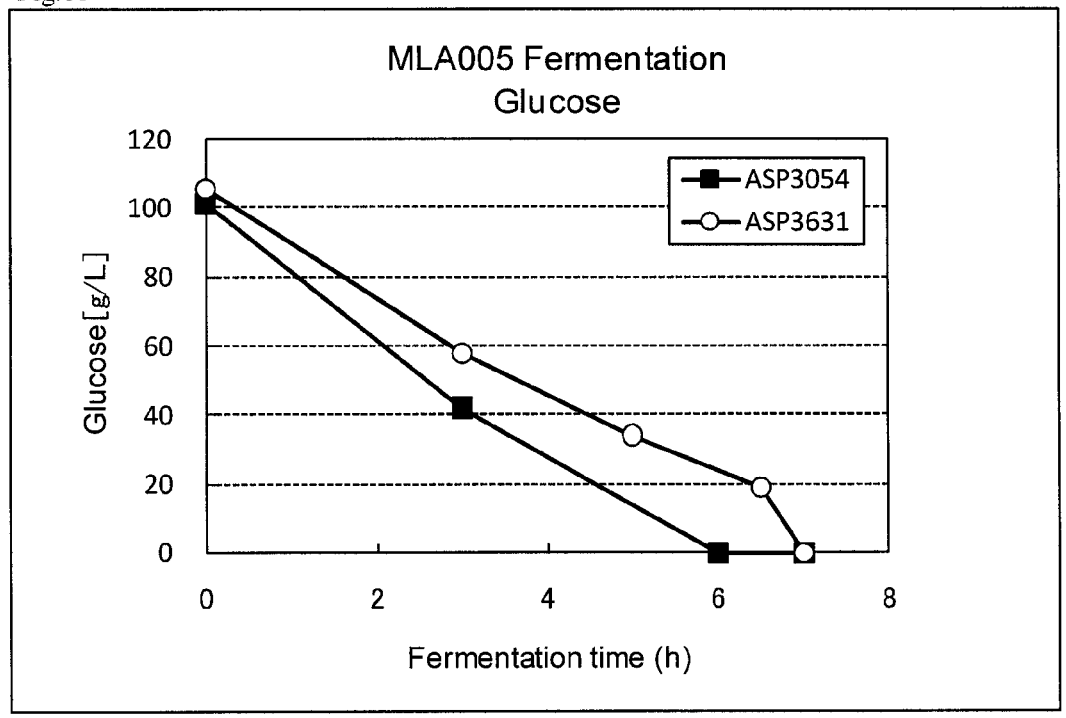
FIG. 11 is a graph showing a change in glucose concentration over time during the test tube fermentation in [Example 3] in Examples.
Figure 12:
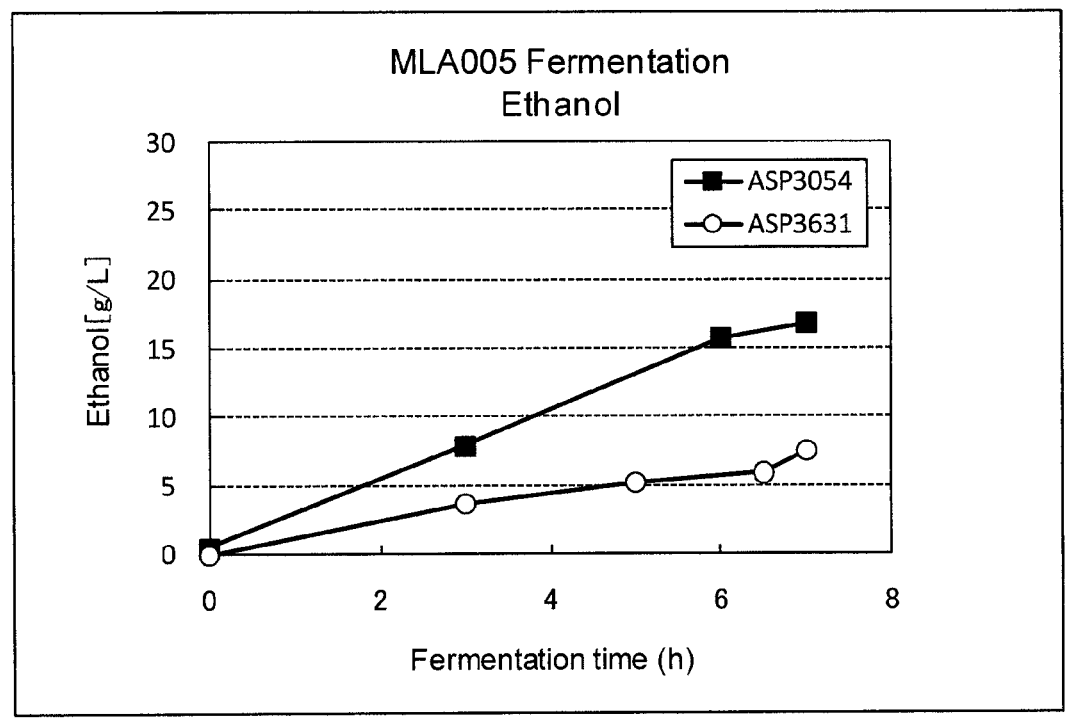
FIG. 12 is a graph showing a change in ethanol concentration over time during the test tube fermentation in [Example 3] in Examples.

In the fermentation test in a test tube, the cells were collected from the culture solution taken out in a small amount from the jar fermenter, and inoculated into 4.5 mL of an 11.1 mass % glucose aqueous solution at an initial cell density of 36 g (dry cell weight basis)/L, and fermentation was carried out for 7 hours under the conditions that the temperature was 32° C. and the shaking rate was 110 rpm. The concentrations (g/L) of lactic acid, glucose, and ethanol in the fermentation solution measured after completion of the fermentation are shown in FIG. 10, FIG. 11, and FIG. 12. Further, the sugar base yield (selectivity %) and the production rate (g/(L·h)) of lactic acid at the time point when all the glucose in the fermentation medium was consumed calculated from the measurement results in the test tube fermentation are shown in Table 15.

TABLE 15

| Strain | Fermentation time [h] | Production rate of lactic acid [g/(lh)] | Sugar base yield of lactic acid [%] |
|---|---|---|---|
| ASP3054 | 6.0 | 12.8 | 76.0 |
| ASP3631 | 7.0 | 13.0 | 86.0 |

In the test tube fermentation test with the cells cultured in the jar fermenter, the ASP3631 strain achieved a lactic acid concentration as high as 90 g/L. It was confirmed that also the cells cultured in the jar fermenter, which is a system closer to the actual production, have an ability to produce lactic acid without any problems. In the ASP3631 strain, the lactic acid production rate was equivalent to that of the ASP3054 strain, and the sugar base yield of lactic acid was higher by about 10% than in the case of the ASP3054 strain. It was considered that due to the improvement of the sugar base yield of lactic acid, the cost advantage of the ASP3631 strain was increased.

While the present invention has been described in detail and with reference to specific embodiments thereof, it will be apparent to one skilled in the art that various changes and modifications can be made therein without departing from the spirit and scope of the present invention.

The invention claimed is:

1. A *Schizosaccharomyces pombe* transformant, wherein the transformant is transformed with a *Lactobacillus pentosus* lactate dehydrogenase gene and a human lactate dehydrogenase gene, and wherein a chromosomal pyruvate decarboxylase (PDC) gene in the transformant is deleted or inactivated, wherein the *Lactobacillus pentosus* lactate dehydrogenase gene and the human lactate dehydrogenase gene are expressed in the transformant, and wherein the transformant produces lactic acid.

2. The transformant according to claim 1, wherein the chromosomal pyruvate decarboxylase gene is PDC2.

3. The transformant according to claim 1, wherein the *Lactobacillus pentosus* lactate dehydrogenase gene and the human lactate dehydrogenase gene are introduced into the chromosome of the transformant.

4. A method for producing the *Schizosaccharomyces pombe* transformant of claim 1 comprising:
transforming a *Schizosaccharomyces pombe* host cell with a vector comprising a *Lactobacillus pentosus* lactate dehydrogenase gene and a vector comprising a human lactate dehydrogenase gene to obtain a transformant,
wherein a chromosomal pyruvate decarboxylase (PDC) gene in the *Schizosaccharomyces pombe* host cell or the transformant is deleted or inactivated, and wherein the transformant is transformed with the human lactate dehydrogenase gene after deleting or inactivating the chromosomal PDC gene or the transformant is transformed with the human lactate dehydrogenase gene prior to deleting or inactivating the chromosomal PDC gene.

5. The method according to claim 4, wherein the vectors comprise a promoter and a terminator which function in *Schizosaccharomyces pombe*.

6. The method according to claim 4, wherein the chromosomal pyruvate decarboxylase gene is PDC2.

7. The method according to claim 4, wherein the vectors further comprise a recombination region for carrying out a homologous recombination for the chromosome of the *Schizosaccharomyces pombe* host cell, and the *Lactobacillus pentosus* lactate dehydrogenase gene and the human lactate dehydrogenase gene are introduced into the chromosome of the *Schizosaccharomyces pombe* host cell.

8. A method for producing lactic acid, comprising culturing the transformant according to claim 1 in a culture solution and obtaining lactic acid from the culture solution.

9. The method according to claim 8, wherein the culture solution comprises of 1 to 50% by mass in concentration of glucose.

10. The method according to claim 8, wherein the culturing is continued after the pH of the culture solution becomes 3.5 or less due to the lactic acid produced by the transformant.

11. The method according to claim 8, wherein the initial cell density of the transformant in the culture solution is 0.1 to 5 g/L on a dry cell weight basis.

12. The method according to claim 8, wherein the culturing is continued without neutralizing the lactic acid in the culture solution, which was produced by the transformant.

13. The method according to claim 8, wherein the lactic acid is separated from the culture solution without neutralizing the lactic acid in the culture solution, which was produced by the transformant.

* * * * *

SEQUENCE LISTING

```
<160> NUMBER OF SEQ ID NOS: 41

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: UF

<400> SEQUENCE: 1
ctctccagct ccatccataa g                                                 21

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: UR

<400> SEQUENCE: 2
gacacaactt cctaccaaaa agcctttctg cccatgtttt ctgtc                       45

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: OF

<400> SEQUENCE: 3 gcttttggt aggaagttgt gtc                                                23

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: OR

<400> SEQUENCE: 4
```
agtgggattt gtagctaagc tgtatccatt tcagccgttt gtg            43

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DF

<400> SEQUENCE: 5
aagtttcgtc aatatcacaa gctgacagaa aacatgggca gaaag          45

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR

<400> SEQUENCE: 6
gttccttaga aaaagcaact ttgg                                  24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FF

<400> SEQUENCE: 7
cataagcttg ccaccacttc                                       20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FR

<400> SEQUENCE: 8
gaaaaagcaa ctttggtatt ctgc                                  24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F for ura4 fragment

<400> SEQUENCE: 9
agcttagcta caaatcccac t                                     21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: R for ura4 fragment

<400> SEQUENCE: 10

| agcttgtgat attgacgaaa ctt | 23 |
|---|---|

<210> SEQ ID NO 11
<211> LENGTH: 6312
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pXLT-TL2

<400> SEQUENCE: 11

| actagtgaat tcgagtatgt gtacgagttg tctttaaacc cacagaggta gaatgtatat | 60 |
|---|---|
| ataaaattaa taagctaagt gtaatactta aaaatacat taattggaac tcgtatccta | 120 |
| ccatttacaa tgttcatcca atttttttcag attgtactgt aaatagcgtt tgaaaacacc | 180 |
| aaatttttaga agctaatcac tctcatcata atcgtctaca tcctcatcgt tatcgacgat | 240 |
| aaaagaatca tcttgcatgc tgggttcatc catgctatca aacgagggat caacgtaaat | 300 |
| aggtgttttc actgtagccg ctgctcttct ggttggcctc tttctaatcg gagaatctga | 360 |
| atcttctggt ggctctgcgt tagtcgaact agcttttgga gttgaactac tacctggaat | 420 |
| aataaaatca tcatcgtcat cttcaggtga ttgtttcttt accgagcttg cttttttccc | 480 |
| tttattcttc gcagaagcct tcgtggatgt tatggtggaa ggtttcaaac tgctaggcaa | 540 |
| caaatcatct tcatcgtctg aagaaaatat ggtagtagca actggtttat tagtctttct | 600 |
| tcctcttcca gacgccgagg ctgctatttt tttgacgggt tttttactac ctgcgtcttc | 660 |
| agagtcaaca gattgacttc ttttttcttga ttttccacta tcactgctat ccaatcccgg | 720 |
| gctcttagat atgcgatttt cttcaactga taagccatga gagttatcct ctgtcttgac | 780 |
| aatgtttatg tcagatgatt tctcaggttc tttcgacgct gcgaactcaa gtaaagtttg | 840 |
| ttgctttcga tttgttgtag atggtttgga ttcgctgcta gcttctttttt taacagcagt | 900 |
| acttgaggag gatccggcaa tagccctggg tttcctagta ccagtggatt tacctcgagg | 960 |
| cttcttttc gttcgattta caaaatctct tgaggattgc tcttcttcta acatttctct | 1020 |
| ctgaatatca tccataacct tattccaagc atgctcaaat gcatccaaat catgaagcca | 1080 |
| caattcttta ggagtttttt taatcaaagc atccagttcg gccattactt cgtccttttt | 1140 |
| cttgagaagt tccacatacc gttcataggt caaagaccat aaaggcattg aaagaaggta | 1200 |
| attgtaggca tctgaatcct cgtcttgcga acatcacca gattgttctt cttcagcaag | 1260 |
| agcatttca acttctaaat caaccaaatg cccttttcttt ggtttactga taggttgaaa | 1320 |
| cttctttttcc ttcagctcca caatgagatc cttttttcttc tttttttgaaa ctacaagctc | 1380 |
| cccctctata atcatatgaa taaaccgcgc ttgatttgaa aatctatcaa accttttttc | 1440 |
| caattcatta accatatgct ctttacgtct ctggtatgtc cttaaacgta cttcgtaaaa | 1500 |
| ctcggtcaaa atatcttcaa cactgtcata cttcttgatc cgtccagatg catcaaaagc | 1560 |

```
aatcatatta ctcgttgctt gagtacgcga cagtttaaac ttaacttcca aggattcatt    1620
taatgcttct ttcatgccag cttcggtaag cgtgacatta agtgaacatt ttccttcacc    1680
gtgatggctt tcatagtcca cgatgaattt acgaattttt tccgtaccaa caagaccagc    1740
ctccagatac tccttcattc gtacgtggct taactatgcg gcatcagagc agattgtact    1800
gagagtgcac catatgcggt gtgaaatacc gcacagatgc gtaaggagaa ataccgcat     1860 caggcgctct tccgcttcct cgctcactga ctcgctgcgc tcggtcgttc ggctgcggcg    1920
agcggtatca gctcactcaa aggcggtaat acggttatcc acagaatcag gggataacgc    1980
aggaaagaac atgcatgtga gcaaaaggcc agcaaaaggc caggaaccgt aaaaaggccg    2040
cgttgctggc gtttttccat aggctccgcc cccctgacga gcatcacaaa aatcgacgct    2100
caagtcagag gtggcgaaac ccgacaggac tataaagata ccaggcgttt ccccctggaa    2160
gctccctcgt gcgctctcct gttccgaccc tgccgcttac cggatacctg tccgcctttc    2220
tcccttcggg aagcgtggcg ctttctcata gctcacgctg taggtatctc agttcggtgt    2280
aggtcgttcg ctccaagctg ggctgtgtgc acgaaccccc cgttcagccc gaccgctgcg    2340
ccttatccgg taactatcgt cttgagtcca acccggtaag acacgactta tcgccactgg    2400
cagcagccac tggtaacagg attagcagag cgaggtatgt aggcggtgct acagagttct    2460
tgaagtggtg gcctaactac ggctacacta aaggacagt atttggtatc tgcgctctgc    2520
tgaagccagt taccttcgga aaagagttg gtagctcttg atccggcaaa caaccaccg    2580 ctggtagcgg tggtttttt gtttgcaagc agcagattac gcgcagaaaa aaaggatctc    2640
aagaagatcc tttgatcttt tctacggggt ctgacgctca gtggaacgaa aactcacgtt    2700
aagggatttt ggtcatgaga ttatcaaaaa ggatcttcac ctagatcctt ttaaattaaa    2760
aatgaagttt taaatcaatc taagtatat atgagtaaac ttggtctgac agttaccaat    2820
gcttaatcag tgaggcacct atctcagcga tctgtctatt tcgttcatcc atagttgcct    2880
gactccccgt cgtgtagata actacgatac gggagggctt accatctggc cccagtgctg    2940
caatgatacc gcgagaccca cgctcaccgg ctccagattt atcagcaata aaccagccag    3000
ccggaagggc cgagcgcaga agtggtcctg caactttatc cgcctccatc cagtctatta    3060
attgttgccg ggaagctaga gtaagtagtt cgccagttaa tagtttgcgc aacgttgttg    3120
ccattgctgc aggcatcgtg gtgtcacgct cgtcgtttgg tatggcttca ttcagctccg    3180
gttcccaacg atcaaggcga gttacatgat cccccatgtt gtgcaaaaaa gcggttagct    3240
ccttcggtcc tccgatcgtt gtcagaagta agttggccgc agtgttatca ctcatggtta    3300
tggcagcact gcataattct cttactgtca tgccatccgt aagatgcttt tctgtgactg    3360
gtgagtactc aaccaagtca ttctgagaat agtgtatgcg gcgaccgagt tgctcttgcc    3420
cggcgtcaac acgggataat accgcgccac atagcagaac tttaaaagtg ctcatcattg    3480
gaaaacgttc ttcggggcga aaactctcaa ggatcttacc gctgttgaga tccagttcga    3540
tgtaacccac tcgtgcaccc aactgatctt cagcatcttt tactttcacc agcgtttctg    3600
ggtgagcaaa aacaggaagg caaaatgccg caaaaaaggg aataagggcg acacggaaat    3660
gttgaatact catactcttc ctttttcaat attattgaag catttatcag ggttattgtc    3720
tcatgagcgg atacatattt gaatgtattt agaaaaataa acaaataggg gttccgcgca    3780
catttccccg aaaagtgcca cctgacgtct aagaaaccat tattatcatg acattaacct    3840
ataaaaatag gcgtatcacg aggccctttc gtcttcaaga attgttgttc gtacggcggc    3900
ttcgatagct tcagcctcct taggagcatt caaaccataa cgaaggagaa gggaagcaga    3960
```

```
taaaattgta ccaacaggat taacaatgcc cttgccagcg atatcgggag cgctaccgtg    4020
aatgggctca accaaacaat gaaccttttc ttctgatttt cctaccacac cggaaaggga    4080
ggcagaaggc aaaaggccca agctaccagg aatgacagaa gcctcatctg aaataatgtc    4140
accaaacaag ttgtcagtca aaacaacacc gttaagtgta cgagggctct tgaccaaaag    4200
catggctgcg gagtcaatga gctggttttt taaggtaagg tgaggatatt cctccttaaa    4260
aatcttagct acagtcttgc gccaaagacg agaagttgcc aaaacattag ctttgtcgag    4320
taatgtgacg ggagcaggag ggttggaagt ttcagctaac caagcagcca acgagcaat     4380 acgagaaact tcttccaaac tgtaaggcca agtgtccata gcataacccg atccgttgtc    4440
ctcagtgcgc tcaccaaagt aacaacctcc agtaagttct cgtacaacac aaaaatcgac    4500
accttcaacg atttcaggct tcaaagggct gtacttgact aaagacttgc tggcaaagtt    4560
gcaaggtcga aggttggccc aaacacccat actcttacga agcttcaata aaccttgctc    4620
aggacgacaa ttggggttgg tccattcagg accaccaacg gcacccaaaa gaacaccgtc    4680
agcttccaaa caagccttca cagtctcgtc agtcaaaggg gttccatagg catcaataga    4740
ggcacctcca atcttgtgtt cttcaaactc gagttttaac tcaggtcgct tcttctcaac    4800
gactttcaaa acctccaagg cagaagcaac aatttcaggg ccaatatggt ctcctggtaa    4860
gacgacgatt ttcttttgcac acatgttgtt gaagaagttt tgttgtgaaa tggtttcgtg    4920
aaagtttcag accctaccgc aaaaatgcct ggtttcggga aactcaacac tgttgcactt    4980
tttatactac agattgggat atcgataata ttgcgtaaaa aatccttttt ttaaaaagct    5040
tgtttacagt aacgtaaatg accagaaatc agatgaaaat cacaagaaag caaataattc    5100
acgttaaatc ctgatatgtt tgattttgtg atgaaatcat ggatgttcat aggaattgtt    5160
gaaattgcgc tttttaacg aaatatacaa gtatcctgga gcttacttaa ttaattaatg     5220
aatctttgtt tctagttatt aatagtaatc aattacgggg tcattagttc atagcccata    5280
tatggagttc cgcgttacat aacttacggt aaatggcccg cctggctgac cgcccaacga    5340
cccccgccca ttgacgtcaa taatgacgta tgttcccata gtaacgccaa tagggacttt    5400
ccattgacgt caatgggtgg agtatttacg gtaaactgcc cacttggcag tacatcaagt    5460
gtatcatatg ccaagtacgc cccctattga cgtcaatgac ggtaaatggc ccgcctggca    5520
ttttgcccag tacatgacct tatgggactt tcctacttgg cagtacatct acgtattagt    5580
catcgctatt accatggtga tgcggttttg gcagtacatc aatgggcgtg gatagcggtt    5640
tgactcacgg gatttccaa gtctccaccc cattgacgtc aatgggagtt tgttttggca     5700
ccaaaatcaa cgggactttc caaaatgtcg taacaactcc gccccattga cgcaaatggg    5760
cggtaggcgt gtacggtggg aggtctatat aagcagattt ctctttagtt ctttgcaaga    5820
aggtagagat aaagacactt tttcaaacat gtgaagcagg tgtcggtacc cggggatcct    5880
ctagagtcga cctgcaggca tgcaagctta aataggaaag tttcttcaac aggattacag    5940
tgtagctacc tacatgctga aaaatatagc ctttaaatca tttttatatt ataactctgt    6000
ataatagaga taagtccatt ttttaaaaat gttttcccca accataaaa ccctatacaa      6060 gttgttctag taacaataca tgagaaagat gtctatgtag ctgaaaataa aatgacgtca    6120
caagacgatc tgcctcgcgc gtttcggtga tgacggtgaa aacctctgac acatgcagct    6180
cccggagacg tcacagcttg tctgtaagcg gatgccggg agcagacaag cccgtcaggg     6240
cgcgtcagcg ggtgttggcg ggtgtcgggg cgcagccatg acccagtcac gtagcgatag    6300
```
cggagtgtag gc                                                       6312

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HsLDH-F

<400> SEQUENCE: 12
aaaaccatgg caactctaaa ggatcagctg atttat                             36

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HsLDH-R

<400> SEQUENCE: 13
aaaaggtacc ttaaaattgc agctcctttt ggatccc                            37

<210> SEQ ID NO 14
<211> LENGTH: 332
<212> TYPE: PRT
<213> ORGANISM: Homo sapiens
<220> FEATURE:
<223> OTHER INFORMATION: HsLDH

<400> SEQUENCE: 14

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly

```
            195                 200                 205
Val Ser Leu Lys Thr Leu His Pro Asp Leu Gly Thr Asp Lys Asp Lys
210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
        275                 280                 285

Leu Ser Val Pro Cys Ile Leu Gly Gln Asn Gly Ile Ser Asp Leu Val
    290                 295                 300

Lys Val Thr Leu Thr Ser Glu Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LpLDH-F

<400> SEQUENCE: 15
aaaaccatgt caagcatgcc aaatcatcaa aaag                                34

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LpLDH-R

<400> SEQUENCE: 16
aaaaggtacc ttatttgttt tctaattctg ctaaaccgtc g                        41

<210> SEQ ID NO 17
<211> LENGTH: 320
<212> TYPE: PRT
<213> ORGANISM: Lactobacillus pentosus
<220> FEATURE:
<223> OTHER INFORMATION: LpLDH

<400> SEQUENCE: 17

Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
```

```
                65                  70                  75                  80
Thr Ala Gly Ala Pro Gln Lys Pro Gly Glu Ser Arg Leu Asp Leu Val
                    85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Glu Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Asp Asp Leu Ala Lys Leu Glu Asp Gly Val Arg Asn Lys Ala Tyr Asp
210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Ile Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LbLDH-F

<400> SEQUENCE: 18 caatttatt tataaacaat gagtagaaaa gtcctgctgg ttg                    43

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LbLDH-R

<400> SEQUENCE: 19
ctctagagga tccccggtta tcctaaagag tccagggttg cc                    42

<210> SEQ ID NO 20
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LplLDH-F

<400> SEQUENCE: 20 gacactttt caaacatgat ggataagaag caacgcaaag tc                   42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LplLDH-R

<400> SEQUENCE: 21
catgtgaagc aggtgttatg atgccacatt catcatggtc ag                   42

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PaLDH-F

<400> SEQUENCE: 22 gacactttt caaacatgat gtctaatatt caaaatcatc aaaaagttgt cc          52

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PaLDH-R

<400> SEQUENCE: 23
catgtgaagc aggtgttatt tgtcttgttt ttcagcaaga gcg                   43

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SaLDH-F

<400> SEQUENCE: 24 gacactttt caaacatgat gaaaacattt ggtaaaaagg ttgtattaat cg          52

<210> SEQ ID NO 25
<211> LENGTH: 62
<212> TYPE: DNA
<213> ORGANISM: Artificial Sequence
<220> FEATURE:
```

-continued

<223> OTHER INFORMATION: Description of Artificial Sequence: Synthetic
     oligonucleotide
<220> FEATURE:
<223> OTHER INFORMATION: SaLDH-R

<400> SEQUENCE: 25
catgtgaagc aggtgttagt cttctaataa atatttaatt gaatcaaatg tatcttctaa    60
tg    62

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Tf2-2-F

<400> SEQUENCE: 26
aaggcctcgt acgtgaaagc aagagcaaaa cga    33

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Tf2-2-R

<400> SEQUENCE: 27
aaggcctcgt acgtgctttg tccgcttgta gc    32

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: MCS-Tf2-2-F

<400> SEQUENCE: 28
ggggtaccaa gcttctagag tcgactccgg tgctacgaca cttt    44

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: MCS-Tf2-2-R

<400> SEQUENCE: 29
ggggtaccag gcctctcgag gctagccatt tccagcgtac atcct    45

<210> SEQ ID NO 30
<211> LENGTH: 7816
<212> TYPE: DNA
<213> ORGANISM: Artificial Sequence
<220> FEATURE:
<223> OTHER INFORMATION: Description of Artificial Sequence: Synthetic
     polynucleotide <220> FEATURE:
<223> OTHER INFORMATION: pTf2(MCS)-ura4

<400> SEQUENCE: 30

```
gtacgtggct taactatgcg gcatcagagc agattgtact gagagtgcac catatgcggt      60
gtgaaatacc gcacagatgc gtaaggagaa ataccgcat caggcgctct tccgcttcct     120
cgctcactga ctcgctgcgc tcggtcgttc ggctgcggcg agcggtatca gctcactcaa     180
aggcggtaat acggttatcc acagaatcag gggataacgc aggaaagaac atgcatgtga     240
gcaaaaggcc agcaaaaggc caggaaccgt aaaaaggccg cgttgctggc gtttttccat     300
aggctccgcc cccctgacga gcatcacaaa aatcgacgct caagtcagag gtggcgaaac     360
ccgacaggac tataaagata ccaggcgttt ccccctggaa gctccctcgt gcgctctcct     420
gttccgaccc tgccgcttac cggatacctg tccgcctttc tcccttcggg aagcgtggcg     480
ctttctcata gctcacgctg taggtatctc agttcggtgt aggtcgttcg ctccaagctg     540
ggctgtgtgc acgaaccccc cgttcagccc gaccgctgcg ccttatccgg taactatcgt     600
cttgagtcca acccggtaag acacgactta tcgccactgg cagcagccac tggtaacagg     660
attagcagag cgaggtatgt aggcggtgct acagagttct tgaagtggtg cctaactac     720
ggctacacta gaaggacagt atttggtatc tgcgctctgc tgaagccagt taccttcgga     780
aaaagagttg gtagctcttg atccggcaaa caaaccaccg ctggtagcgg tggtttttt     840
gtttgcaagc agcagattac gcgcagaaaa aaaggatctc aagaagatcc tttgatcttt     900
tctacggggt ctgacgctca gtggaacgaa aactcacgtt aagggatttt ggtcatgaga     960
ttatcaaaaa ggatcttcac ctagatcctt ttaaattaaa aatgaagttt taaatcaatc    1020
taaagtatat atgagtaaac ttggtctgac agttaccaat gcttaatcag tgaggcacct    1080
atctcagcga tctgtctatt tcgttcatcc atagttgcct gactccccgt cgtgtagata    1140
actacgatac gggagggctt accatctggc cccagtgctg caatgatacc gcgagaccca    1200
cgctcaccgg ctccagattt atcagcaata aaccagccag ccggaagggc cgagcgcaga    1260
agtggtcctg caactttatc cgcctccatc cagtctatta attgttgccg ggaagctaga    1320
gtaagtagtt cgccagttaa tagtttgcgc aacgttgttg ccattgctgc aggcatcgtg    1380
gtgtcacgct cgtcgtttgg tatggcttca ttcagctccg gttcccaacg atcaaggcga    1440
gttacatgat cccccatgtt gtgcaaaaaa gcggttagct ccttcggtcc tccgatcgtt    1500
gtcagaagta agttggccgc agtgttatca ctcatggtta tggcagcact gcataattct    1560
cttactgtca tgccatccgt aagatgcttt tctgtgactg gtgagtactc aaccaagtca    1620
ttctgagaat agtgtatgcg gcgaccgagt tgctcttgcc cggcgtcaac acgggataat    1680
accgcgccac atagcagaac tttaaaagtg ctcatcattg gaaaacgttc ttcggggcga    1740
aaactctcaa ggatcttacc gctgttgaga tccagttcga tgtaacccac tcgtgcaccc    1800
aactgatctt cagcatcttt tactttcacc agcgtttctg ggtgagcaaa aacaggaagg    1860
caaaatgccg caaaaaaggg aataagggcg acacggaaat gttgaatact catactcttc    1920
ctttttcaat attattgaag catttatcag ggttattgtc tcatgagcgg atacatattt    1980
gaatgtattt agaaaaataa acaaataggg gttccgcgca catttccccg aaaagtgcca    2040
cctgacgtct aagaaaccat tattatcatg acattaacct ataaaaatag gcgtatcacg    2100
aggccctttc gtcttcaaga attgttgttc gtacgtgaaa gcaagagcaa aacgatggag    2160
accagagaat ttggatggaa ttcaaacatc agacgaacat ttaataaacc ttttttgcaaa   2220
```

```
aatattatcg aagcatgtac cagagatagg gaaattcgat cctaataagg atgttgaaag    2280
ttacatttca aaacttgatc aacactttac tgaatacect tcattattcc caaatgagca    2340
tactaaaaga cagtatacat tgaatcacct agaagaatta gagcaacaat tcgctgaacg    2400
catgttttct gagaatggaa gtcttacatg gcaagaatta ctcagacaaa cagggaaagt    2460
acaaggatcc aacaaaggtg atcgtttaac taaaacattt gaaggtttta gaaatcaatt    2520
ggacaaagtt caatttataa ggaaactcat gtcaaaagca aatgttgatg atttccatac    2580
tcgcttgttt atattatgga tgctgccata ttccttaagg aaattaaagg aaagaaatta    2640
ctggaaatca gaaatcagtg aaatttatga cttttagag gacaaaagaa cagcctcgta    2700
tggtaaaact cacaagcgtt ttcaactgca aaataaaaat ctaggaaaag agtccctttc    2760
aaagaaaaat aacaccacta atagcagaaa cctgaggaag acaaatgttt cgagaataga    2820
atactcatct aacaaattcc taaatcatac taggaaacgt tacgaaatgg tattacaagc    2880
tgaacttcca gacttcaagt gctcaatacc ctgtctaatc gatacgggcg ctcaagcaaa    2940
tattataaca gaagaaactg ttcgagcaca taaactgcct accagaccct ggtcaaaaag    3000
tgtgatatat ggtggagttt atccaaataa gattaatcgc aaaacaataa aacttaacat    3060
aagtctaaat ggaatatcaa tcaaaacaga attcttggtt gtaaagaaat tttcgcatcc    3120
agctgctatc tccttcacaa cattatatga caataacatt gaaatatcta gcagtaaaca    3180
cacgctctct caaatgaaca aagtttcaaa tattgtcaag gaacctgagt taccagatat    3240
ctataaagaa ttcaaagaca ttactgcaga aaccaatacg gaaaagctac caaagccaat    3300
aaaagggtta gaatttgaag ttgaactaac tcaagaaaac tacagattac ctatcagaaa    3360
ttacccgcta ccaccgggaa aaatgcaagc tatgaatgat gaaattaatc aaggattaaa    3420
aagtggaatt atacgagaat ctaaagccat taacgcctgt ccagtaatgt tcgttccgaa    3480
aaaggaaggc accttgagaa tggtggttga ctacaaacct ttaaataagt atgtcaaacc    3540
caatatatat ccgttaccac ttattgaaca attacttgct aaaatacaag gttctacaat    3600
ttttactaaa cttgacctca aaagtgccta tcacttgata cgagtaagaa aaggagatga    3660
acataaactt gcttttcgct gtcctcgtgg agttttgaa tatctagtaa tgccttatgg    3720
catatctaca gctccagcac attttcaata ctttatcaat acaatacttg gtgaagccaa    3780
agaatcacat gtagtatgtt tatgggatga tatttaatt cattcaaaat cggaatctga    3840
acatgtaaaa catgttaaag acgttctaca gaaattgaaa aatgcgaact taattatcaa    3900
tcaagcaaaa tgtgaatttc accaatcaca agtaaaattt atagggtatc acatttcgga    3960
aaaaggattt acgccttgtc aagaaaatat agacaaagtc ttacaatgga agcaacctaa    4020
gaatcgtaaa gaattcgac aatttctagg ttctgtcaat tatcttagga aattcattcc    4080
aaagacatca caattaacac atccactcaa taatcttttg aaaaaggatg tacgctggaa    4140
atggctagcc tcgagaggcc tggtaccaag cttgtgatat tgacgaaact ttttgacatc    4200
taatttattc tgttccaaca ccaatgttta taaccaagtt ttatcttgtt tgtctacatg    4260
gtattttaca ttcatctaca tacatctttc attggctttg tacatagtta tcattacaag    4320
tctaaaaaaa ttcactcttt tcttattcaa tgtcaatcca agagaaaaga ttgtggtaat    4380
gttgtaggag catgtttaat aaattactat agcaaattac tttttattcc caaggtgttt    4440
atctataata gttaatattt tagtcgctac ataaaatttt accaaagagt acttgtatac    4500
taattctaaa tgccttctga cataaaacgc ctaggaaaac aaacgcaaac aaggcatcga    4560
ctttttcaat aaccaaccaa aaaaatttta cattagtctt tttttaatgc tgagaaagtc    4620
```

-continued

```
tttgctgata tgccttccaa ccagcttctc tatatctctt ggcttcgaca acaggattac    4680
gaccagctcc atagactcca cgaccaacaa tgatgatatc gctaccgcag tttacaatca    4740
cttcttcagg agtacgatat tgctgtccca gcccgtctcc tttaacatcc aagccgatac    4800
caggggacat agttatgtag tcgctttgaa ggttaggaaa tcgacgacca gctataaagc    4860
caaagcaaaa atcggtatgc ttctcaaacc attctaaggt tttctctgtg taggaaccag    4920
tagccaaaga gcctttggaa gacatttcag ccaaaagcaa gagaccacgt cccaaaggta    4980
aaccaacttc tttgaggcct tgtataatac cctcgcctgg cactgtatgg caatttgtga    5040
tatgagccca agaagcaatt ttgtacacac cagatgcata ttgtagcttg acggtatttc    5100
caatgtctgc gaatttgcga tcctcaaaga taagaaaacg atgcttttta cctaaggcca    5160
ccagtttttc taccatatcc tggtcgaaat cctcgacaac gtcaatatgt gtcttgataa    5220
cacagacata gggtccaatt ttatctacca attctaagat ttcggatttc ttcgtcaaat    5280
cgaccgcgac tgacaagttg ctttgctttt cttccatcaa agccaacaat tccttggcaa    5340
tgggattttt catcccctca gctctagctg aatagctttg aaatactcta gcatccataa    5400
ctttgctttt aaacctttaa tttcgatcca agcaaaaaag aggttcttgg taggacaata    5460
cggtaagaaa acacgacatg tgcagagatg ccgacgaagc atagttaaac tgggatggta    5520
aaatcaatta agaatttata aagacaaaat tgtataagtc tctaaaacat cttaattata    5580
cctcacagaa ctatctaaaa tatattcaca aagtgcaaac attatcatga aaaagaacca    5640
ttttaattta aagcaagggc attaaggctt atttacagaa tttcttactt ttgtaaagat    5700
tataaggctg attatctttt tcaccatgcc aaaaattaca caagatagaa tggatgtttg    5760
aaattaaacg tgagtataca aacaaataca ctaggtaaat cgaaacattt ttttctccat    5820
taagtaacaa attcctattt agagaaagaa tgctgagtag attaaataat ctatacaaac    5880 tttttaaca caaatgcata catatagcca gtgggatttg tagctaagct tctagagtcg    5940
actccggtgc tacgacactt tgatttcagt aaaaagattc tactggaaac tgatgcttca    6000
gatgtcgctg taggagccgt attgtctcaa aaacatgatg atgataaata ctatcctgtt    6060
ggatactatt cagcaaagat gtctaaagca caattaaatt atagcgtatc ggacaaagaa    6120
atgcttgcaa tcattaagtc tctcaaacat tggagacact atttagaatc cactatcgaa    6180
cctttcaaaa ttttaacaga ccatcgaaac ttaattggtc gcattactaa cgaatccgag    6240
cctgaaaaca aacgtttagc tcgttggcaa ttattttac aagacttcaa ctttgaaatt    6300
aactacagac ctggatcagc aaatcacata gctgatgcct tatccagaat tgttgacgaa    6360
acagaaccaa ttccaaaaga ttcagaagac aatagtatca actttgttaa tcaaatctcg    6420
ataaccgatg atttttaaaaa ccaagtggtt acagaatata cgaatgatac aaaattgttg    6480
aatttactaa acaatgaaga caaacgagtg gaagagaata tccaactcaa agatggctta    6540
ctaattaaca gtaaagacca aatcttatta cctaatgata ctcagctgac taggacaatt    6600
attaaaaagt atcatgaaga aggtaaattg attcatccag gcattgaact tcttacaaac    6660
attatattac gtagatttac gtggaaagga ataagaaaac aaatacaaga atatgtacag    6720
aactgccata catgtcaaat aaacaaatct aggaatcata accctatgg accttttacaa    6780 ccaattcccc catcagaaag accttgggaa tctttatcaa tggatttat tacagcttta    6840 ccagaatcat ctggttataa tgcactttc gtggtagttg accgattttc aaaaatggca    6900
atcttagtac cttgtacgaa atccattaca gcagagcaaa cagctcgaat gtttgatcaa    6960
```

```
cgagttattg cttatttcgg caatccaaaa gaaatcattg cagataatga tcatattttt    7020
acttcccaaa cgtggaaaga tttcgcacat aaatataatt tcgttatgaa attttcgtta    7080
ccatacagac cacaaactga tggacaaact gagcgtacaa accaaactgt ggagaaatta    7140
ctaagatgtg tatgtagcac acatccaaat acatgggtag atcatatatc cctagtgcaa    7200
caatcttaca acaatgcgat acattcagca actcaaatga cacctttttga gatagtacat   7260 cgctattcac cagctttatc accttttagag ttacctagct ttagtgacaa aactgacgaa   7320
aactctcagg aaacgatcca agtatttcaa acagttaaag aacacttgaa tacaaacaac    7380
ataaagatga aaaagtattt cgatatgaaa atacaagaaa ttgaagaatt tcaacctgga    7440
gacctagtta tggtcaaaag aacgaaaaca ggttttcttc ataaatccaa taaattagca    7500
cctagttttg caggaccgtt ctatgtgtta cagaagtcgg gtccaaacaa ctatgaattg    7560
gatcttccag attcaatcaa gcacatgttt tcatctactt ttcatgtttc tcacctagaa    7620
aagtatcgac ataattcaga actcaattac gctaccattg atgagtctga tattggaaca    7680
attcttcata tcctagaaca taaaaacaga gaacaagtac tctacttaaa tgtcaagtac    7740
atttcgaatc taaatccgag tactattatg tcaggatgga ctacattagc tacagcgcta    7800
caagcggaca aagcac                                                   7816

<210> SEQ ID NO 31
<211> LENGTH: 5960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pSL6

<400> SEQUENCE: 31
aacccacaga ggtagaatgt atatataaaa ttaataagct aagtgtaata cttaaaaaat      60
acattaattg gaactcgtat cctaccattt acaatgttca tccaattttt tcagattgta     120
ctgtaaatag cgtttgaaaa caccaaattt tagaagctaa tcactctcat cataatcgtc     180
tacatcctca tcgttatcga cgataaaaga atcatcttgc atgctgggtt catccatgct     240
atcaaacgag ggatcaacgt aaataggtgt tttcactgta gccgctgctc ttctggttgg     300 cctcttttcta atcggagaat ctgaatcttc tggtggctct cgttagtcg aactagcttt      360 tggagttgaa ctactacctg gaataataaa atcatcatcg tcatcttcag gtgattgttt     420
ctttaccgag cttgcttttt tcccttattt cttcgcagaa gccttcgtgg atgttatggt     480
ggaaggtttc aaactgctag gcaacaaatc atcttcatcg tctgaagaaa atatggtagt     540
agcaactggt ttattagtct ttcttcctct tccagacgcc gaggctgcta tttttttgac     600 gggttttta ctacctgcgt cttcagagtc aacagattga cttctttttc ttgattttcc      660
actatcactg ctatccaatc ccgggctctt agatatgcga ttttcttcaa ctgataagcc    720
atgagagtta tcctctgtct tgacaatgtt tatgtcagat gatttctcag gttctttcga    780
cgctgcgaac tcaagtaaag tttgttgctt tcgatttgtt gtagatggtt tggattcgct    840
gctagcttct ttttttaacag cagtacttga ggaggatccg gcaatagccc tgggtttcct   900
agtaccagtg gatttaccctc gaggcttctt tttcgttcga tttacaaaat ctcttgagga   960
ttgctcttct tctaacattt ctctctgaat atcatcccata accttattcc aagcatgctc  1020
aaatgcatcc aaatcatgaa gccacaattc tttaggagtt ttttttaatca aagcatccag  1080
```

```
ttcggccatt acttcgtcct tttcttgag aagttccaca taccgttcat aggtcaaaga    1140
ccataaaggc attgaaagaa ggtaattgta ggcatctgaa tcctcgtctt gcgaaacatc    1200
accagattgt tcttcttcag caagagcatt ttcaacttct aaatcaacca atgcccttt     1260 ctttggttta ctgataggtt gaaacttctt ttccttcagc tccacaatga gatccttttt    1320
cttctttttt gaaactacaa gctcccctc tataatcata tgaataaacc gcgcttgatt    1380
tgaaaatcta tcaaaccttt tttccaattc attaaccata tgctctttac gtctctggta    1440
tgtccttaaa cgtacttcgt aaaactcggt caaaatatct tcaacactgt catacttctt    1500
gatccgtcca gatgcatcaa aagcaatcat attactcgtt gcttgagtac gcgacagttt    1560
aaacttaact tccaaggatt catttaatgc ttctttcatg ccagcttcgg taagcgtgac    1620
attaaagtga acatttcctt caccgtgatg gctttcatag tccacgatga atttacgaat    1680
tttttccgta ccaacaagac cagcctccag atactccttc attcgtacga tttaaatgcg    1740
gccgcttcgg ctgcggcgag cgggtatcag ctcactcaaa ggcggtaata cggttatcca    1800
cagaatcagg ggataacgca ggaaagaaca tgtgagcaaa aggccagcaa aaggccagga    1860
accgtaaaaa ggccgcgttg ctggcgtttt tccataggct ccgcccccct gacgagcatc    1920
acaaaaatcg acgctcaagt cagaggtggc gaaacccgac aggactataa agataccagg    1980
cgtttccccc tggaagctcc ctcgtgcgct ctcctgttcc gaccctgccg cttaccggat    2040
acctgtccgc ctttctccct tcgggaagcg tggcgctttc tcaatgctca cgctgtaggt    2100
atctcagttc ggtgtaggtc gttcgctcca agctgggctg tgtgcacgaa ccccccgttc    2160
agcccgaccg ctgcgcctta tccggtaact atcgtcttga gtccaacccg gtaagacacg    2220
acttatcgcc actggcagca gccactggta acaggattag cagagcgagg tatgtaggcg    2280
gtgctacaga gttcttgaag tggtggccta actacggcta cactagaagg acagtatttg    2340
gtatctgcgc tctgctgaag ccagttacct tcggaaaaag agttggtagc tcttgatccg    2400
gcaaacaaac caccgctggt agcggtggtt tttttgtttg caagcagcag attacgcgca    2460
gaaaaaaagg atctcaagaa gatcctttga tcttttctac ggggtctgac gctcagtgga    2520
acgaaaactc acgttaaggg attttggtca tgagcttgcg ccgtcccgtc aagtcagcgt    2580
aatgctctgc cagtgttaca accaattaac caattctgat tagaaaaact catcgagcat    2640
caaatgaaac tgcaatttat tcatatcagg attatcaata ccatattttt gaaaaagccg    2700
tttctgtaat gaaggagaaa actcaccgag gcagttccat aggatggcaa gatcctggta    2760
tcggtctgcg attccgactc gtccaacatc aatacaacct attaatttcc ctcgtcaaa     2820 aataaggtta tcaagtgaga aatcaccatg agtgacgact gaatccggtg agaatggcaa    2880
gagcttatgc atttctttcc agacttgttc aacaggccag ccattacgct cgtcatcaaa    2940
atcactcgca tcaaccaaac cgttattcat tcgtgattgc gcctgagcga ggcgaaatac    3000
gcgatcgctg ttaaaaggac aattacaaac aggaatcgaa tgcaaccggc gcaggaacac    3060
tgccagcgca tcaacaatat tttcacctga atcaggatat tcttctaata cctggaatgc    3120
tgttttccca gggatcgcag tggtgagtaa ccatgcatca tcaggagtac ggataaaatg    3180
cttgatggtc ggaagaggca taaattccgt cagccagttt agtctgacca tctcatctgt    3240
aacatcattg gcaacgctac ctttgccatg tttcagaaac aactctggcg catcgggctt    3300
cccatacaat cggtagattg tcgcacctga ttgcccgaca ttatcgcgag cccatttata    3360
cccatataaa tcagcatcca tgttggaatt taatcgcggc ctcgtcgagc aagacgtttc    3420
ccgttgaata tggctcataa caccccttgt attactgttt atgtaagcag acagttttat    3480
```

```
tgttcattta aatgcggccg cgtacggcgg cttcgatagc ttcagcctcc ttaggagcat    3540
tcaaaccata acgaaggaga agggaagcag ataaaattgt accaacagga ttaacaatgc    3600
ccttgccagc gatatcggga gcgctaccgt gaatgggctc aaccaaacaa tgaaccttt     3660 cttctgattt tcctaccaca ccggaaaggg aggcagaagg caaaaggccc aagctaccag    3720
gaatgacaga agcctcatct gaaataatgt caccaaacaa gttgtcagtc aaaacaacac    3780
cgttaagtgt acgagggctc ttgaccaaaa gcatggctgc ggagtcaatg agctggtttt    3840
ttaaggtaag gtgaggatat tcctccttaa aaatcttagc tacagtcttg cgccaaagac    3900
gagaagttgc caaaacatta gctttgtcga gtaatgtgac gggagcagga gggttggaag    3960
tttcagctaa ccaagcagcc aaacgagcaa tacgagaaac ttcttccaaa ctgtaaggcc    4020
aagtgtccat agcataaccc gatccgttgt cctcagtgcg ctcaccaaag taacaacctc    4080
cagtaagttc tcgtacaaca caaaaatcga caccttcaac gatttcaggc ttcaaagggc    4140
tgtacttgac taaagacttg ctggcaaagt tgcaaggtcg aaggttggcc caaacaccca    4200
tactcttacg aagcttcaat aaaccttgct caggacgaca attggggttg gtccattcag    4260
gaccaccaac ggcacccaaa agaacaccgt cagcttccaa acaagccttc acagtctcgt    4320
cagtcaaagg ggttccatag gcatcaatag aggcacctcc aatcttgtgt tcttcaaact    4380
cgagttttaa ctcaggtcgc ttcttctcaa cgactttcaa aacctccaag gcagaagcaa    4440
caatttcagg gccaatatgg tctcctggta agacgacgat tttctttgca cacatgttgt    4500
tgaagaagtt ttgttgtgaa atggttttcgt gaaagtttca gaccctaccg caaaaatgcc    4560
tggtttcggg aaactcaaca ctgttgcact tttatacta cagattggga tatcgataat    4620
attgcgtaaa aaatcctttt tttaaaaagc ttgtttacag taacgtaaat gaccagaaat    4680
cagatgaaaa tcacaagaaa gcaaataatt cacgttaaat cctgatatgt ttgattttgt    4740
gatgaaatca tggatgttca taggaattgt tgaaattgcg cttttttaac gaaatataca    4800
agtatcctgg agcttactta attaattaat gaatctttgt tcctaggccc gggctagtaa    4860
tcaattacgg ggtcattagt tcatagccca tatatggagt tccgcgttac ataacttacg    4920
gtaaatggcc cgcctggctg accgcccaac gacccccgcc cattgacgtc aataatgacg    4980
tatgttccca tagtaacgcc aatagggact ttccattgac gtcaatgggt ggagtattta    5040
cggtaaactg cccacttggc agtacatcaa gtgtatcata tgccaagtac gccccctatt    5100
gacgtcaatg acggtaaatg gcccgcctgg cattttgccc agtacatgac cttatgggac    5160
tttcctactt ggcagtacat ctacgtatta gtcatcgcta ttaccatggt gatgcggttt    5220
tggcagtaca tcaatgggcg tggatagcgg tttgactcac ggggatttcc aagtctccac    5280
cccattgacg tcaatgggag tttgttttgg caccaaaatc aacgggactt tccaaaatgt    5340
cgtaacaact ccgccccatt gacgcaaatg ggcggtaggc gtgtacggtg ggaggtctat    5400
ataagcagat ttctctttag ttcttttgcaa gaaggtagag ataaagacac tttttcaaac    5460
atgtgaagca ggtgtcggta cccggggatc ctctagagtc gacctgcagg catgcaagct    5520
taaataggaa agtttcttca acaggattac agtgtagcta cctacatgct gaaaaatata    5580
gcctttaaat catttttata ttataactct gtataataga gataagtcca ttttttaaaa    5640
atgttttccc caaaccataa aaccctatac aagttgttct agtaacaata catgagaaag    5700
atgtctatgt agctgaaaat aaaatgacgt cacaagacga tctgcctcgc gcgtttcggt    5760
gatgacggtg aaaacctctg acacatgcag ctcccggaga cggtcacagc ttgtctgtaa    5820
```

```
gcggatgccg ggagcagaca agcccgtcag ggcgcgtcag cgggtgttgg cgggtgtcgg    5880
ggcgcagcca tgacccagtc acgtagcgat agcggagccc gggcactagt gaattcgagt    5940
atgtgtacga gttgtcttta                                                5960

<210> SEQ ID NO 32
<211> LENGTH: 501
<212> TYPE: DNA
<213> ORGANISM: Schizosaccharomyces pombe
<220> FEATURE:
<223> OTHER INFORMATION: ihc1 promoter

<400> SEQUENCE: 32
tggcttcaac tagctcggga tgatatccca tattttatgc ccgacaccgt ttgtcatccg      60
cttagtcgtg atacccgtct gccacatagc gaatgtcaaa ggattatgct actttacgtg     120
agaatgaaat atagacttta cacatcgcca catgatggca tcgatagagc tgctagtttc     180
aattactttc aattaacgag tgaaaagcgg atgtaccgca tcatctgttg agcgaaatag     240
tctacgtaaa atcaaatggg ctaatttgtc gctgaattaa cccaaaagca aaatacgat      300 tgcaattctc attacgaaat gctgaatggg atggaaaata aattgatgtc acaatttccg     360
aggactctta caaatattat atatagagca cggggtacat cactatcgat tcgaattttc     420
aagaagtaat atttcgcacc gtagtacttt ttgtaagccg ttttattaaa tcagaaagaa     480
ctccaatttt atttataaac a                                               501

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ihc1-promoter-F

<400> SEQUENCE: 33
aattcctagg ggcttcaact agctcgggat                                       30

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ihc1-promoter-R

<400> SEQUENCE: 34
aattggtacc gacacctgct tcacattgtt tataaataaa attggagtt                  49

<210> SEQ ID NO 35
<211> LENGTH: 5847
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pSL12

<400> SEQUENCE: 35
gaatgtatat ataaaattaa taagctaagt gtaatactta aaaatacat taattggaac       60
```

-continued

```
tcgtatccta ccatttacaa tgttcatcca attttttcag attgtactgt aaatagcgtt       120
tgaaaacacc aaattttaga agctaatcac tctcatcata atcgtctaca tcctcatcgt       180
tatcgacgat aaaagaatca tcttgcatgc tgggttcatc catgctatca aacgagggat       240
caacgtaaat aggtgttttc actgtagccg ctgctcttct ggttggcctc tttctaatcg       300
gagaatctga atcttctggt ggctctgcgt tagtcgaact agcttttgga gttgaactac       360
tacctggaat aataaaatca tcatcgtcat cttcaggtga ttgtttcttt accgagcttg       420
cttttttccc tttattcttc gcagaagcct tcgtggatgt tatggtggaa ggtttcaaac       480
tgctaggcaa caaatcatct tcatcgtctg aagaaaatat ggtagtagca actggtttat       540
tagtctttct tcctcttcca gacgccgagg ctgctatttt tttgacgggt tttttactac       600
ctgcgtcttc agagtcaaca gattgacttc ttttttcttga ttttccacta tcactgctat       660
ccaatcccgg gctcttagat atgcgatttt cttcaactga taagccatga gagttatcct       720
ctgtcttgac aatgtttatg tcagatgatt tctcaggttc tttcgacgct gcgaactcaa       780
gtaaagtttg ttgctttcga tttgttgtag atggtttgga ttcgctgcta gcttcttttt       840
taacagcagt acttgaggag gatccggcaa tagccctggg tttcctagta ccagtggatt       900
tacctcgagg cttcttttc gttcgattta caaaatctct tgaggattgc tcttcttcta       960
acatttctct ctgaatatca tccataacct tattccaagc atgctcaaat gcatccaaat      1020
catgaagcca caattcttta ggagtttttt taatcaaagc atccagttcg gccattactt      1080
cgtccttttt cttgagaagt tccacatacc gttcataggt caaagaccat aaaggcattg      1140
aaagaaggta attgtaggca tctgaatcct cgtcttgcga acatcacca gattgttctt       1200 cttcagcaag agcattttca acttctaaat caaccaaatg ccctttcttt ggtttactga      1260
taggttgaaa cttctttcc ttcagctcca caatgagatc ttttttcttc ttttttgaaa       1320
ctacaagctc cccctctata atcatatgaa taaaccgcgc ttgatttgaa aatctatcaa      1380
accttttttc caattcatta accatatgct ctttacgtct ctggtatgtc cttaaacgta      1440
cttcgtaaaa ctcggtcaaa atatcttcaa cactgtcata cttcttgatc cgtccagatg      1500
catcaaaagc aatcatatta ctcgttgctt gagtacgcga cagtttaaac ttaacttcca      1560
aggattcatt taatgcttct ttcatgccag cttcggtaag cgtgacatta aagtgaacat      1620
ttccttcacc gtgatggctt tcatagtcca cgatgaattt acgaattttt tccgtaccaa      1680
caagaccagc ctccagatac tccttcattc gtacgattta aatgcggccg cttcggctgc      1740
ggcgagcggg tatcagctca ctcaaaggcg gtaatacggt tatccacaga atcagggggat      1800 aacgcaggaa agaacatgtg agcaaaaggc cagcaaaagg ccaggaaccg taaaaaggcc      1860
gcgttgctgg cgttttttcca taggctccgc cccccctgacg agcatcacaa aaatcgacgc      1920
tcaagtcaga ggtggcgaaa cccgacagga ctataaagat accaggcgtt tccccctgga      1980
agctccctcg tgcgctctcc tgttccgacc ctgccgctta ccggatacct gtccgccttt      2040
ctcccttcgg gaagcgtggc gctttctcaa tgctcacgct gtaggtatct cagttcggtg      2100
taggtcgttc gctccaagct gggctgtgtg cacgaacccc ccgttcagcc cgaccgctgc      2160
gccttatccg gtaactatcg tcttgagtcc aacccggtaa gacacgactt atcgccactg      2220
gcagcagcca ctggtaacag gattagcaga gcgaggtatg taggcggtgc tacagagttc      2280
ttgaagtggt ggcctaacta cggctacact agaaggacag tatttggtat ctgcgctctg      2340
ctgaagccat taccttcgg aaaaagagtt ggtagctctt gatccggcaa acaaaccacc      2400
gctggtagcg gtggtttttt tgtttgcaag cagcagatta cgcgcagaaa aaaaggatct      2460
```

```
caagaagatc ctttgatctt ttctacgggg tctgacgctc agtggaacga aaactcacgt    2520
taagggattt tggtcatgag cttgcgccgt cccgtcaagt cagcgtaatg ctctgccagt    2580
gttacaacca attaaccaat tctgattaga aaaactcatc gagcatcaaa tgaaactgca    2640
atttattcat atcaggatta tcaataccat attttttgaaa aagccgtttc tgtaatgaag    2700
gagaaaactc accgaggcag ttccatagga tggcaagatc ctggtatcgg tctgcgattc    2760
cgactcgtcc aacatcaata caacctatta atttcccctc gtcaaaaata aggttatcaa    2820
gtgagaaatc accatgagtg acgactgaat ccggtgagaa tggcaagagc ttatgcattt    2880
ctttccagac ttgttcaaca ggccagccat tacgctcgtc atcaaaatca ctcgcatcaa    2940
ccaaaccgtt attcattcgt gattgcgcct gagcgaggcg aaatacgcga tcgctgttaa    3000
aaggacaatt acaaacagga atcgaatgca accggcgcag gaacactgcc agcgcatcaa    3060
caatattttc acctgaatca ggatattctt ctaatacctg aatgctgtt tcccaggga    3120 tcgcagtggt gagtaaccat gcatcatcag gagtacggat aaaatgcttg atggtcggaa    3180
gaggcataaa ttccgtcagc cagtttagtc tgaccatctc atctgtaaca tcattggcaa    3240
cgctaccttt gccatgtttc agaaacaact ctggcgcatc gggcttccca tacaatcggt    3300
agattgtcgc acctgattgc ccgacattat cgcgagccca tttatacccca tataaatcag    3360 catccatgtt ggaatttaat cgcggcctcg tcgagcaaga cgtttcccgt tgaatatggc    3420
tcataacacc ccttgtatta ctgtttatgt aagcagacag ttttattgtt catttaaatg    3480
cggccgcgta cggcggcttc gatagcttca gcctccttag gagcattcaa accataacga    3540
aggagaaggg aagcagataa aattgtacca acaggattaa caatgccctt gccagcgata    3600
tcgggagcgc taccgtgaat gggctcaacc aaacaatgaa cctttcttc tgattttcct    3660 accacaccgg aaagggaggc agaaggcaaa aggcccaagc taccaggaat gacagaagcc    3720
tcatctgaaa taatgtcacc aaacaagttg tcagtcaaaa caacaccgtt aagtgtacga    3780
gggctcttga ccaaaagcat ggctgcggag tcaatgagct ggttttttaa ggtaaggtga    3840
ggatattcct ccttaaaaat cttagctaca gtcttgcgcc aaagacgaga agttgccaaa    3900
acattagctt tgtcgagtaa tgtgacggga gcaggagggt tggaagtttc agctaaccaa    3960
gcagccaaac gagcaatacg agaaacttct tccaaactgt aaggccaagt gtccatagca    4020
taacccgatc cgttgtcctc agtgcgctca ccaaagtaac aacctccagt aagttctcgt    4080
acaacacaaa aatcgacacc ttcaacgatt tcaggcttca aagggctgta cttgactaaa    4140
gacttgctgg caaagttgca aggtcgaagg ttggcccaaa cacccatact cttacgaagc    4200
ttcaataaac cttgctcagg acgacaattg gggttggtcc attcaggacc accaacggca    4260
cccaaaagaa caccgtcagc ttccaaacaa gccttcacag tctcgtcagt caagggggtt    4320
ccataggcat caatagaggc acctccaatc ttgtgttctt caaactcgag ttttaactca    4380
ggtcgcttct tctcaacgac tttcaaaacc tccaaggcag aagcaacaat tcagggcca    4440 atatggtctc ctggtaagac gacgattttc tttgcacaca tgttgttgaa gaagttttgt    4500
tgtgaaatgg tttcgtgaaa gtttcagacc ctaccgcaaa aatgcctggt tcgggaaac    4560 tcaacactgt tgcacttttt atactacaga ttggatatc gataatattg cgtaaaaaat    4620 cctttttttta aaagcttgt ttacagtaac gtaaatgacc agaaatcaga tgaaaatcac    4680
aagaaagcaa ataattcacg ttaaatcctg atatgtttga ttttgtgatg aaatcatgga    4740
tgttcatagg aattgttgaa attgcgcttt tttaacgaaa tatacaagta tcctggagct    4800
```

```
tacttaatta attaatgaat ctttgttcct aggggcttca actagctcgg gatgatatcc    4860 catatttat gcccgacacc gtttgtcatc cgcttagtcg tgatacccgt ctgccacata    4920
gcgaatgtca aaggattatg ctactttacg tgagaatgaa atatagactt tacacatcgc    4980
cacatgatgg catcgataga gctgctagtt tcaattactt tcaattaacg agtgaaaagc    5040
ggatgtaccg catcatctgt tgagcgaaat agtctacgta aaatcaaatg gctaatttg    5100 tcgctgaatt aacccaaaag caaaaatacg attgcaattc tcattacgaa atgctgaatg    5160
ggatggaaaa taaattgatg tcacaatttc cgaggactct tacaaatatt atatatagag    5220
cacggggtac atcactatcg attcgaattt tcaagaagta atatttcgca ccgtagtact    5280
ttttgtaagc cgttttatta aatcagaaag aactccaatt ttatttataa acaatgtgaa    5340
gcaggtgtcg gtacccgggg atcctctaga gtcgacctgc aggcatgcaa gcttaaatag    5400
gaaagtttct tcaacaggat tacagtgtag ctacctacat gctgaaaaat atagccttta    5460
aatcattttt atattataac tctgtataat agagataagt ccattttta aaaatgtttt    5520 ccccaaacca taaaccccta tacaagttgt tctagtaaca atacatgaga aagatgtcta    5580
tgtagctgaa aataaaatga cgtcacaaga cgatctgcct cgcgcgtttc ggtgatgacg    5640
gtgaaaacct ctgacacatg cagctcccgg agacggtcac agcttgtctg taagcggatg    5700
ccgggagcag acaagcccgt cagggcgcgt cagcgggtgt tggcgggtgt cggggcgcag    5760
ccatgaccca gtcacgtagc gatagcggag cccgggcact agtgaattcg agtatgtgta    5820
cgagttgtct ttaaacccac agaggta                                         5847
```

<210> SEQ ID NO 36
<211> LENGTH: 200
<212> TYPE: DNA
<213> ORGANISM: Schizosaccharomyces pombe
<220> FEATURE:
<223> OTHER INFORMATION: ihc1 terminator

<400> SEQUENCE: 36

```
ttgctgccca gttgattacc cgtcattgct ttgatgtgtc tgaagtatct tcagttttga     60
ttttatgttg ttaatacaga attccatagt aatgatgagt atacatgttt atgatcttat    120
gaatattatt tcattcacca gctttaact tttgaaaccg ttgtccttgt agaagtagtc    180
gacaccccat agcatacaat                                                 200
```

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ihc1-terminator-F

<400> SEQUENCE: 37

```
cctgcaggca tgcaagctta ttgctgccca gttgattacc c                          41
```

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ihc1-terminator-R

```
<400> SEQUENCE: 38
gaaacgcgcg aggcagatca ttgtatgcta tggggtgtcg ac                                42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pSL12-F

<400> SEQUENCE: 39
gtcgacaccc catagcatac aatgatctgc ctcgcgcgtt tc                                42

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pSL12-R

<400> SEQUENCE: 40
gggtaatcaa ctgggcagca ataagcttgc atgcctgcag g                                 41

<210> SEQ ID NO 41
<211> LENGTH: 5831
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pSL17

<400> SEQUENCE: 41
gaatgtatat ataaaattaa taagctaagt gtaatactta aaaatacat taattggaac              60 tcgtatccta ccatttacaa tgttcatcca attttttcag attgtactgt aaatagcgtt            120
tgaaaacacc aaatttttaga agctaatcac tctcatcata atcgtctaca tcctcatcgt           180
tatcgacgat aaaagaatca tcttgcatgc tgggttcatc catgctatca aacgagggat            240
caacgtaaat aggtgttttc actgtagccg ctgctcttct ggttggcctc tttctaatcg            300
gagaatctga atcttctggt ggctctgcgt tagtcgaact agcttttgga gttgaactac            360
tacctggaat aataaaatca tcatcgtcat cttcaggtga ttgtttcttt accgagcttg            420
cttttttccc tttattcttc gcagaagcct tcgtggatgt tatggtggaa ggtttcaaac            480
tgctaggcaa caaatcatct tcatcgtctg aagaaaatat ggtagtagca actggtttat            540
tagtctttct tcctcttcca gacgccgagg ctgctatttt tttgacgggt ttttactac             600 ctgcgtcttc agagtcaaca gattgacttc ttttttcttga ttttccacta tcactgctat           660
ccaatcccgg gctcttagat atgcgatttt cttcaactga taagccatga gagttatcct            720
ctgtcttgac aatgtttatg tcagatgatt tctcaggttc tttcgacgct gcgaactcaa            780
gtaaagtttg ttgctttcga tttgttgtag atggtttgga ttcgctgcta gcttcttttt            840
taacagcagt acttgaggag gatccggcaa tagccctggg tttcctagta ccagtggatt            900
tacctcgagg cttctttttc gttcgattta caaaatctct tgaggattgc tcttcttcta            960
```

```
acatttctct ctgaatatca tccataacct tattccaagc atgctcaaat gcatccaaat    1020
catgaagcca caattcttta ggagtttttt taatcaaagc atccagttcg gccattactt    1080
cgtccttttt cttgagaagt tccacatacc gttcataggt caaagaccat aaaggcattg    1140
aaagaaggta attgtaggca tctgaatcct cgtcttgcga acatcacca gattgttctt     1200 cttcagcaag agcattttca acttctaaat caaccaaatg ccctttcttt ggtttactga    1260
taggttgaaa cttcttttcc ttcagctcca caatgagatc ttttttcttc tttttttgaaa  1320 ctacaagctc ccctctata atcatatgaa taaaccgcgc ttgatttgaa aatctatcaa    1380
accttttttc caattcatta accatatgct ctttacgtct ctggtatgtc cttaaacgta    1440
cttcgtaaaa ctcggtcaaa atatcttcaa cactgtcata cttcttgatc cgtccagatg    1500
catcaaaagc aatcatatta ctcgttgctt gagtacgcga cagtttaaac ttaacttcca    1560
aggattcatt taatgcttct ttcatgccag cttcggtaag cgtgacatta aagtgaacat    1620
ttccttcacc gtgatggctt tcatagtcca cgatgaattt acgaattttt tccgtaccaa    1680
caagaccagc ctccagatac tccttcattc gtacgattta aatgcggccg cttcggctgc    1740
ggcgagcggg tatcagctca ctcaaaggcg gtaatacggt tatccacaga atcagggggat   1800 aacgcaggaa agaacatgtg agcaaaaggc cagcaaaagg ccaggaaccg taaaaaggcc    1860
gcgttgctgg cgttttttcca taggctccgc cccctgacg agcatcacaa aaatcgacgc   1920
tcaagtcaga ggtggcgaaa cccgacagga ctataaagat accaggcgtt ccccctgga    1980 agctccctcg tgcgctctcc tgttccgacc ctgccgctta ccggatacct gtccgccttt    2040
ctcccttcgg gaagcgtggc gctttctcaa tgctcacgct gtaggtatct cagttcggtg    2100
taggtcgttc gctccaagct gggctgtgtg cacgaacccc ccgttcagcc cgaccgctgc    2160
gccttatccg gtaactatcg tcttgagtcc aacccggtaa gacacgactt atcgccactg    2220
gcagcagcca ctggtaacag gattagcaga gcgaggtatg taggcggtgc tacagagttc    2280
ttgaagtggt ggcctaacta cggctacact agaaggacag tatttggtat ctgcgctctg    2340
ctgaagccag ttaccttcgg aaaaagagtt ggtagctctt gatccggcaa acaaaccacc    2400
gctggtagcg gtggtttttt tgtttgcaag cagcagatta cgcgcagaaa aaaggatct     2460 caagaagatc ctttgatctt ttctacgggg tctgacgctc agtggaacga aaactcacgt    2520
taagggattt tggtcatgag cttgcgccgt cccgtcaagt cagcgtaatg ctctgccagt    2580
gttacaacca attaaccaat tctgattaga aaaactcatc gagcatcaaa tgaaactgca    2640
atttattcat atcaggatta tcaataccat attttgaaa aagccgtttc tgtaatgaag    2700
gagaaaactc accgaggcag ttccatagga tggcaagatc ctggtatcgg tctgcgattc    2760
cgactcgtcc aacatcaata caacctatta atttcccctc gtcaaaaata aggttatcaa    2820
gtgagaaatc accatgagtg acgactgaat ccggtgagaa tggcaagagc ttatgcattt    2880
cttcccagac ttgttcaaca ggccagccat tacgctcgtc atcaaaatca ctcgcatcaa    2940
ccaaaccgtt attcattcgt gattgcgcct gagcgaggcg aaatacgcga tcgctgttaa    3000
aaggacaatt acaaacagga atcgaatgca accggcgcag gaacactgcc agcgcatcaa    3060
caatattttc acctgaatca ggatattctt ctaatacctg gaatgctgtt ttcccaggga    3120
tcgcagtggt gagtaaccat gcatcatcag gagtacggat aaaatgcttg atggtcggaa    3180
gaggcataaa ttccgtcagc cagtttagtc tgaccatctc atctgtaaca tcattggcaa    3240
cgctaccttt gccatgtttc agaaacaact ctggcgcatc gggcttccca tacaatcggt    3300
```

```
agattgtcgc acctgattgc ccgacattat cgcgagccca tttatacccc tataaatcag   3360
catccatgtt ggaatttaat cgcggcctcg tcgagcaaga cgtttcccgt tgaatatggc   3420
tcataacacc ccttgtatta ctgtttatgt aagcagacag ttttattgtt catttaaatg   3480
cggccgcgta cggcggcttc gatagcttca gcctccttag gagcattcaa accataacga   3540
aggagaaggg aagcagataa aattgtacca acaggattaa caatgccctt gccagcgata   3600
tcgggagcgc taccgtgaat gggctcaacc aaacaatgaa ccttttcttc tgattttcct   3660
accacaccgg aaagggaggc agaaggcaaa aggcccaagc taccaggaat gacagaagcc   3720
tcatctgaaa taatgtcacc aaacaagttg tcagtcaaaa caacaccgtt aagtgtacga   3780
gggctcttga ccaaaagcat ggctgcggag tcaatgagct ggttttttaa ggtaaggtga   3840
ggatattcct ccttaaaaat cttagctaca gtcttgcgcc aaagacgaga agttgccaaa   3900
acattagctt tgtcgagtaa tgtgacggga gcaggagggt tggaagtttc agctaaccaa   3960
gcagccaaac gagcaatacg agaaacttct tccaaactgt aaggccaagt gtccatagca   4020
taacccgatc cgttgtcctc agtgcgctca ccaaagtaac aacctccagt aagttctcgt   4080
acaacacaaa aatcgacacc ttcaacgatt tcaggcttca aagggctgta cttgactaaa   4140
gacttgctgg caaagttgca aggtcgaagg ttggcccaaa cacccatact cttacgaagc   4200
ttcaataaac cttgctcagg acgacaattg gggttggtcc attcaggacc accaacggca   4260
cccaaaagaa caccgtcagc ttccaaacaa gccttcacag tctcgtcagt caaggggtt   4320
ccataggcat caatagaggc acctccaatc ttgtgttctt caaactcgag ttttaactca   4380
ggtcgcttct tctcaacgac tttcaaaacc tccaaggcag aagcaacaat ttcagggcca   4440
atatggtctc ctggtaagac gacgattttc tttgcacaca tgttgttgaa gaagttttgt   4500
tgtgaaatgg tttcgtgaaa gtttcagacc ctaccgcaaa aatgcctggt ttcgggaaac   4560
tcaacactgt tgcactttt atactacaga ttgggatatc gataatattg cgtaaaaaat   4620
cctttttta aaagcttgt ttacagtaac gtaaatgacc agaaatcaga tgaaaatcac   4680
aagaaagcaa ataattcacg ttaaatcctg atatgtttga ttttgtgatg aaatcatgga   4740
tgttcatagg aattgttgaa attgcgcttt tttaacgaaa tatacaagta tcctggagct   4800
tacttaatta attaatgaat ctttgttcct aggggcttca actagctcgg gatgatatcc   4860
catattttat gcccgacacc gtttgtcatc cgcttagtcg tgatacccgt ctgcccacata   4920
gcgaatgtca aaggattatg ctactttacg tgagaatgaa atatagactt tacacatcgc   4980
cacatgatgg catcgataga gctgctagtt tcaattactt tcaattaacg agtgaaaagc   5040
ggatgtaccg catcatctgt tgagcgaaat agtctacgta aaatcaaatg ggctaatttg   5100
tcgctgaatt aacccaaaag caaaaatacg attgcaattc tcattacgaa atgctgaatg   5160
ggatggaaaa taaattgatg tcacaatttc cgaggactct tacaaatatt atatatagag   5220
cacggggtac atcactatcg attcgaattt tcaagaagta atatttcgca ccgtagtact   5280
ttttgtaagc cgttttatta aatcagaaag aactccaatt ttatttataa acaatgtgaa   5340
gcaggtgtcg gtacccgggg atcctctaga gtcgacctgc aggcatgcaa gcttattgct   5400
gcccagttga ttacccgtca ttgctttgat gtgtctgaag tatcttcagt tttgatttta   5460
tgttgttaat acagaattcc atagtaatga tgagtataca tgtttatgat cttatgaata   5520
ttatttcatt caccagcttt taacttttga aaccgttgtc cttgtagaag tagtcgacac   5580
cccatagcat acaatgatct gcctcgcgcg tttcggtgat gacggtgaaa acctctgaca   5640
catgcagctc ccggagacgg tcacagcttg tctgtaagcg gatgccggga gcagacaagc   5700
```

```
ccgtcagggc gcgtcagcgg gtgttggcgg gtgtcggggc gcagccatga cccagtcacg    5760
tagcgatagc ggagcccggg cactagtgaa ttcgagtatg tgtacgagtt gtctttaaac    5820
ccacagaggt a                                                         5831
```